(12) United States Patent
Kim et al.

(10) Patent No.: US 10,071,166 B2
(45) Date of Patent: *Sep. 11, 2018

(54) PROTEIN COMPLEX USING AN IMMUNOGLOBULIN FRAGMENT AND METHOD FOR THE PREPARATION THEREOF

(71) Applicant: HANMI SCIENCE CO., LTD, Gyeonggi-do (KR)

(72) Inventors: Young Min Kim, Yongin-si (KR); Dae Jin Kim, Seoul (KR); Sung Min Bae, Seoul (KR); Chang Ki Lim, Suwon-si (KR); Se Chang Kwon, Seoul (KR); Gwan Sun Lee, Seoul (KR)

(73) Assignee: HANMI SCIENCE CO., LTD., Hwaseong-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/796,135

(22) Filed: Mar. 12, 2013

(65) Prior Publication Data

US 2013/0288333 A1    Oct. 31, 2013

Related U.S. Application Data

(63) Continuation of application No. 12/757,635, filed on Apr. 9, 2010, now abandoned, which is a continuation of application No. 10/535,232, filed as application No. PCT/KR2004/002944 on Nov. 13, 2004, now Pat. No. 7,737,260.

(30) Foreign Application Priority Data

Nov. 13, 2003  (KR) .................. 10-2003-0080299

(51) Int. Cl.
| | |
|---|---|
| C07K 16/46 | (2006.01) |
| C07K 1/107 | (2006.01) |
| A61K 47/48 | (2006.01) |
| C07K 19/00 | (2006.01) |
| C07K 14/505 | (2006.01) |
| C07K 14/535 | (2006.01) |
| C07K 14/56 | (2006.01) |
| C07K 14/61 | (2006.01) |
| A61K 47/68 | (2017.01) |

(52) U.S. Cl.
CPC ........ *A61K 47/48369* (2013.01); *A61K 47/68* (2017.08); *A61K 47/6811* (2017.08); *A61K 47/6813* (2017.08); *A61K 47/6835* (2017.08); *C07K 14/505* (2013.01); *C07K 14/535* (2013.01); *C07K 14/56* (2013.01); *C07K 14/61* (2013.01); *C07K 16/46* (2013.01); *C07K 19/00* (2013.01); *C07K 2317/52* (2013.01); *C07K 2317/732* (2013.01); *C07K 2317/734* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,045,312 A | 9/1991 | Aston et al. |
| 5,116,964 A | 5/1992 | Capon et al. |
| 5,225,538 A | 7/1993 | Capon et al. |
| 5,349,053 A | 9/1994 | Landolfi |
| 5,428,130 A | 6/1995 | Capon et al. |
| 5,447,851 A | 9/1995 | Beutler et al. |
| 5,455,165 A | 10/1995 | Capon et al. |
| 5,514,582 A | 5/1996 | Capon et al. |
| 5,585,097 A | 12/1996 | Bolt et al. |
| 5,605,690 A | 2/1997 | Jacobs et al. |
| 5,650,150 A | 7/1997 | Gillies |
| 5,672,688 A | 9/1997 | Kobayashi et al. |
| 5,712,121 A | 1/1998 | Devos et al. |
| 5,714,147 A | 2/1998 | Capon et al. |
| 5,723,125 A | 3/1998 | Chang et al. |
| 5,843,725 A | 12/1998 | Sledziewski et al. |
| 5,844,099 A | 12/1998 | Stahl et al. |
| 5,908,626 A | 6/1999 | Chang et al. |
| 5,977,310 A | 11/1999 | Namiki et al. |
| 6,018,026 A | 1/2000 | Sledziewshi et al. |
| 6,030,613 A | 2/2000 | Blumberg et al. |
| 6,117,656 A | 9/2000 | Seed |
| 6,165,476 A | 12/2000 | Strom et al. |

(Continued)

FOREIGN PATENT DOCUMENTS

| | | |
|---|---|---|
| EP | 04/64533 B1 | 8/1992 |
| EP | 05/80171 A2 | 1/1994 |

(Continued)

OTHER PUBLICATIONS

Steward et al. The binding affinities of rheumatoid factors interacting eith the Cgamma3 homology region of human IgG. Clin. Exp. Immunol. vol. 15:145-152 (1973).*

(Continued)

*Primary Examiner* — Elizabeth Kemmerer
*Assistant Examiner* — Regina M DeBerry
(74) *Attorney, Agent, or Firm* — Sughrue Mion, PLLC

(57) ABSTRACT

Disclosed are a protein conjugate with improved in vivo duration and stability and the use thereof. The protein conjugate includes a physiologically active polypeptide, a non-peptide polymer and an immunoglobulin Fc fragment. Since the three components are covalently linked, the protein conjugate has extended in vivo duration and enhanced stability for the physiologically active polypeptide. The protein conjugate maintains the in vivo activity at relatively high levels and remarkably increases the serum half-life for the physiologically active polypeptide, with less risk of inducing undesirable immune responses. Thus, the protein conjugate is useful for developing long-acting formulations of various polypeptide drugs.

16 Claims, 18 Drawing Sheets

Specification includes a Sequence Listing.

(56) References Cited

U.S. PATENT DOCUMENTS

| | | |
|---|---|---|
| 6,277,375 B1 | 8/2001 | Ward |
| 6,291,212 B1 | 9/2001 | Sledziewski et al. |
| 6,291,646 B1 | 9/2001 | Sledziewski et al. |
| 6,300,099 B1 | 10/2001 | Sledziewski et al. |
| 6,307,025 B1 | 10/2001 | Hession et al. |
| 6,323,323 B1 | 11/2001 | Sledziewski et al. |
| 6,340,742 B1 | 1/2002 | Burg et al. |
| 6,406,697 B1 | 6/2002 | Capon et al. |
| 6,410,008 B1 | 6/2002 | Strom et al. |
| 6,441,136 B1 | 8/2002 | Pettit |
| 6,444,792 B1 | 9/2002 | Gray et al. |
| 6,451,313 B1 | 9/2002 | Maddon et al. |
| 6,475,983 B1 | 11/2002 | Eid et al. |
| 6,482,919 B2 | 11/2002 | Ledbetter et al. |
| 6,541,610 B1 | 4/2003 | Smith |
| 6,620,413 B1 | 9/2003 | DeSauvage et al. |
| 6,656,728 B1 | 12/2003 | Kavanaught et al. |
| 6,660,843 B1 | 12/2003 | Feige et al. |
| 6,677,136 B2 | 1/2004 | Marshall et al. |
| 6,743,778 B2 | 6/2004 | Kohno |
| 6,756,480 B2 | 6/2004 | Kostenuik et al. |
| 6,797,493 B2 | 9/2004 | Sun et al. |
| 6,900,292 B2 | 5/2005 | Sun et al. |
| 6,979,556 B2 | 12/2005 | Simmons et al. |
| 7,125,843 B2 | 10/2006 | DeFrees |
| 7,166,707 B2 | 1/2007 | Feige et al. |
| 7,189,827 B2 | 3/2007 | Feige et al. |
| 7,736,653 B2 | 6/2010 | Kim et al. |
| 7,737,260 B2 | 6/2010 | Kim et al. |
| 8,124,094 B2 | 2/2012 | Kim et al. |
| 8,163,889 B2 | 4/2012 | Kim et al. |
| 9,186,415 B2 * | 11/2015 | Kim ................. A61K 47/48215 |
| 9,421,244 B2 * | 8/2016 | Kim ..................... A61K 38/215 |
| 9,492,507 B2 * | 11/2016 | Song ....................... A61K 38/28 |
| 2001/0053539 A1 | 12/2001 | Lauffer et al. |
| 2002/0037558 A1 | 3/2002 | Lo et al. |
| 2002/0081664 A1 | 6/2002 | Lo et al. |
| 2003/0039654 A1 | 2/2003 | Kostenuik et al. |
| 2003/0082679 A1 | 5/2003 | Sun et al. |
| 2003/0211078 A1 | 11/2003 | Heavner |
| 2003/0229023 A1 | 12/2003 | Oliner et al. |
| 2004/0181033 A1 | 9/2004 | Han et al. |
| 2005/0163799 A1 | 7/2005 | Mann et al. |
| 2006/0083683 A1 | 4/2006 | Hsei et al. |
| 2006/0094083 A1 | 5/2006 | Choi et al. |
| 2006/0153839 A1 * | 7/2006 | Mohamed .......... C07K 16/1278 424/143.1 |
| 2006/0275254 A1 | 12/2006 | Kim et al. |
| 2007/0041967 A1 | 2/2007 | Jung et al. |
| 2010/0105869 A1 | 4/2010 | Kim et al. |
| 2011/0182919 A1 | 7/2011 | Peters et al. |
| 2013/0022626 A1 * | 1/2013 | Kim et al. ................. 424/179.1 |
| 2013/0028867 A1 * | 1/2013 | Kim et al. ................... 424/85.6 |
| 2013/0028918 A1 * | 1/2013 | Song et al. ................ 424/179.1 |
| 2013/0095090 A1 * | 4/2013 | Song et al. .................. 424/94.2 |

FOREIGN PATENT DOCUMENTS

| | | |
|---|---|---|
| JP | 62-201582 | 9/1987 |
| JP | 06-506218 A | 7/1994 |
| JP | 2002-518522 A | 6/2002 |
| JP | 2003-521925 A | 7/2003 |
| JP | 2004-537262 A | 12/2004 |
| JP | 2005-501052 A | 1/2005 |
| KR | 10-0249572 B1 | 12/1999 |
| KR | 10-0316347 | 11/2001 |
| KR | 2003-0009464 | 1/2003 |
| WO | 90/04413 A1 | 5/1990 |
| WO | 91/16354 A1 | 10/1991 |
| WO | 92/10507 A1 | 6/1992 |
| WO | 97/00319 A2 | 1/1997 |
| WO | 97/24137 A1 | 7/1997 |
| WO | 99/02709 A1 | 1/1999 |
| WO | 00/23472 A2 | 4/2000 |
| WO | 00/40615 A2 | 7/2000 |
| WO | 00/69913 A1 | 11/2000 |
| WO | 01/02440 A1 | 1/2001 |
| WO | 01/57217 A1 | 8/2001 |
| WO | 01/81415 A2 | 11/2001 |
| WO | 01/83527 A2 | 11/2001 |
| WO | 02/46227 A2 | 6/2002 |
| WO | 02/48376 A2 | 6/2002 |
| WO | 02/057435 A2 | 7/2002 |
| WO | 02/060489 A1 | 8/2002 |
| WO | 03/011342 A2 | 2/2003 |
| WO | 03/057134 A2 | 7/2003 |
| WO | 03/076567 A2 | 9/2003 |
| WO | 03/077834 A2 | 9/2003 |
| WO | 2004/101739 A2 | 11/2004 |
| WO | 2004/101740 A2 | 11/2004 |
| WO | 2004/108885 A2 | 12/2004 |
| WO | 2005/001025 A2 | 1/2005 |
| WO | 2005/017148 A1 | 2/2005 |
| WO | 2005/037989 A2 | 4/2005 |
| WO | 2005/073383 A2 | 8/2005 |

OTHER PUBLICATIONS

Burton et alo. The determinatio of molecular-motion parameters from proton-relaxation-enhancement measurements in a number of Gd(III) antibody-fragment complexes. Eur. J. Biochem. vol. 75:445-453 (1977).*

Gombotz et al., "PEGylation: A Tool to Enhance Protein Deliver," 2000, American Chemical Society, pp. 110-123.

Gombotz et al., "Pegylation: A Tool to Enhance Protein Delivery," 1999, American Chemical Society, vol. 40, No. 1, pp. 275-276.

European Patent Office, European Office Action issued in corresponding EP Application No. 04 800 091.3, dated Sep. 7, 2010.

Kitai et al., "Extracellular Production of Human Immunoglobulin G Fc Region (hIgG-Fc) by *Escherichia coli*," Applied Microbiology Biotechnology, 1998, vol. 28, pp. 52-56.

Japanese Patent Office, Japanese Office Action issued in corresponding JP Application No. 2006-539397, dated Sep. 21, 2010.

European Patent Office, European Search Report issued in corresponding EP Application No. 10009129.7, dated Oct. 14, 2010.

Japanese Patent Office, Japanese Office Action issued in corresponding Japanese Application No. 2006-539398, dated May 24, 2011.

Paige et al., "Prolonged Circulation of Recombinant Human Granulocyte-Colony Stimulating Factor by Covalent Linkage to Albumin Through a Heterobifunctional Polyethylene Glycol," Pharmaceutical Research, 1995, vol. 12, No. 12, pp. 1883-1888.

Simmons et al., "Expression of Full-length Immunoglobulins in *Escherichia coli*: Rapid and Efficient Production of Aglycosylated Antibodies," 2002, Journal of Immunological Methods, vol. 263, pp. 133-147.

Champman, "PEGylated antibodies and antibody fragments for improved therapy: A review." Advanced Drug Delivery Reviews 54(4): 531-545, Jun. 17, 2002.

Matsuda, et al., "Proton nuclear magnetic resonance studies of the structure of the Fc fragment of humanimmunoglobulin G1: comparisons of native and recombinant proteins," Molecular Immunology 27(6):571-580, 1990.

Stevenson et al., "Conjugation of human Fcγ in closed-hinge or open-hinged configuration to Fab'y and analogous ligands," J. Immunology 158:2242-2250, Jan. 1, 1997.

Bentz, et al., "Improved local delivery of TGF-Beta2 by binding to injectable fibrillar collagen via difunctional polyethylene glycol," J. Biomed. Mat. Res. 39(4):539-548, 1998.

van der Poll, Tom et al., "Effect of a Recombinant Dimeric Tumor Necrosis Factor receptor on Inflammatory Responses to Intravenous Endotoxin in Normal Humans," Blood 89(10): 3727-3734, May 15, 2997.

* cited by examiner

M: Molecular size marker
Lane 1: Fc
Lane 2: Physiologically active protein
Lane 3: Physiologically active protein-PEG-Fc conjugate

SEQUENCE LISTING

<160> NUMBER OF SEQ ID NOS: 8

<210> SEQ ID NO 1
<211> LENGTH: 35
<212> TYPE: DNA
<213> ORGANISM: Artificial Sequence
<220> FEATURE:
<223> OTHER INFORMATION: Synthetic construct

<400> SEQUENCE: 1
cgtcatgccc agcacctgag ttcctggggg gacca                                    35

<210> SEQ ID NO 2
<211> LENGTH: 42
<212> TYPE: DNA
<213> ORGANISM: Artificial Sequence
<220> FEATURE:
<223> OTHER INFORMATION: Synthetic construct

<400> SEQUENCE: 2
gggggatcct catttaccca gagacaggga gaggctcttc tg                            42

<210> SEQ ID NO 3
<211> LENGTH: 29
<212> TYPE: DNA
<213> ORGANISM: Artificial Sequence
<220> FEATURE:
<223> OTHER INFORMATION: Synthetic construct

<400> SEQUENCE: 3
cggcacctga gttcctgggg ggaccatca                                           29

<210> SEQ ID NO 4
<211> LENGTH: 69
<212> TYPE: DNA
<213> ORGANISM: Homo sapiens

<400> SEQUENCE: 4
atgaaaaaga caatcgcatt tcttcttgca tctatgttcg ttttttctat tgctacaaat         60
gcccaggcg                                                                 69

<210> SEQ ID NO 5
<211> LENGTH: 45
<212> TYPE: DNA
<213> ORGANISM: Artificial Sequence

```
<220> FEATURE:
<223> OTHER INFORMATION: Synthetic construct

<400> SEQUENCE: 5
tctattgcta caaatgccca ggccttccca accattccct tatcc            45

<210> SEQ ID NO 6
<211> LENGTH: 45
<212> TYPE: DNA
<213> ORGANISM: Artificial Sequence
<220> FEATURE:
<223> OTHER INFORMATION: Synthetic construct

<400> SEQUENCE: 6
agataacgat gtttacgggt ccggaagggt tggtaaggga atagg            45

<210> SEQ ID NO 7
<211> LENGTH: 36
<212> TYPE: DNA
<213> ORGANISM: Artificial Sequence
<220> FEATURE:
<223> OTHER INFORMATION: Synthetic construct

<400> SEQUENCE: 7
gagtccaaat atggtccccc atgcccatca tgccca                      36

<210> SEQ ID NO 8
<211> LENGTH: 12
<212> TYPE: PRT
<213> ORGANISM: Artificial Sequence
<220> FEATURE:
<223> OTHER INFORMATION: Synthetic construct of hinge region of IgG4

<400> SEQUENCE: 8

Glu Ser Lys Tyr Gly Pro Pro Cys Pro Ser Cys Pro
 1               5                   10
```

PROTEIN COMPLEX USING AN IMMUNOGLOBULIN FRAGMENT AND METHOD FOR THE PREPARATION THEREOF

This is a continuation application of U.S. Ser. No. 12/757,635 filed Apr. 9, 2010, which is a continuation application of U.S. Ser. No. 10/535,232 filed on Jun. 19, 2006 (U.S. Pat. No. 7,737,260), which is a national stage application under 35 U.S.C. 371 of PCT/KR2004/002944 filed on Nov. 13, 2004, which claims priority from Korean patent application 10-2003-0080299 filed on Nov. 13, 2003.

TECHNICAL FIELD

The present invention relates to a protein conjugate comprising a physiologically active polypeptide, a non-peptide polymer and an immunoglobulin Fc fragment, which are covalently linked and have an extended duration of physiological action compared to the native form.

BACKGROUND ART

Since polypeptides tend to be easily denatured due to their low stability, degraded by proteolytic enzymes in the blood and easily passed through the kidney or liver, protein medicaments, including polypeptides as pharmaceutically effective components, need to be frequently administered to patients to maintain desired blood level concentrations and titers. However, this frequent administration of protein medicaments, especially through injection, causes pain for patients. To solve these problems, many efforts have been made to improve the serum stability of protein drugs and maintain the drugs in the blood at high levels for a prolonged period of time, and thus maximize the pharmaceutical efficacy of the drugs. Pharmaceutical compositions with sustained activity, therefore need to increase the stability of the protein drugs and maintain the titers at sufficiently high levels without causing immune responses in patients.

To stabilize proteins and prevent enzymatic degradation and clearance by the kidneys, a polymer having high solubility, such as polyethylene glycol (hereinafter, referred to simply as "PEG"), was conventionally used to chemically modify the surface of a protein drug. By binding to specific or various regions of a target protein, PEG stabilizes the protein and prevents hydrolysis, without causing serious side effects (Sada et al., *J. Fermentation Bioengineering* 71: 137-139, 1991). However, despite its capability to enhance protein stability, this PEG coupling has problems such as greatly reducing the number titers of physiologically active proteins. Further, the yield decreases with the increasing molecular weight of the PEG due to the reduced reactivity of the proteins.

Recently, polymer-protein drug conjugates have been suggested. For example, as described in U.S. Pat. No. 5,738,846, a conjugate can be prepared by linking an identical protein drug to both ends of PEG to improve the activity of the protein drug. Also, as described in International Pat. Publication No. WO 92/16221, two different protein drugs can be linked to both ends of PEG to provide a conjugate having two different activities. The above methods, however, were not very successful in sustaining the activity of protein drugs.

On the other hand, Kinstler et al. reported that a fusion protein prepared by coupling granulocyte-colony stimulating factor (G-CSF) to human albumin showed improved stability (Kinstler et al., *Pharmaceutical Research* 12(12): 1883-1888, 1995). In this publication, however, since the modified drug, having a G-CSF-PEG-albumin structure, only showed an approximately four-fold increase in residence time in the body and a slight increase in serum half-life compared to the single administration of the native G-CSF, it has not been industrialized as an effective long-acting formulation for protein drugs.

An alternative method for improving the in vivo stability of physiologically active proteins is by linking a gene of physiologically active protein to a gene encoding a protein having high serum stability by genetic recombination technology and culturing the cells transfected with the recombinant gene to produce a fusion protein. For example, a fusion protein can be prepared by conjugating albumin, a protein known to be the most effective in enhancing protein stability, or its fragment to a physiologically active protein of interest by genetic recombination (International Pat. Publication Nos. WO 93/15199 and WO 93/15200, European Pat. Publication No. 413,622). A fusion protein of interferon-alpha and albumin, developed by the Human Genome Science Company and marketed under the trade name of 'Albuferon™', increased the half-life from 5 hours to 93 hours in monkeys, but it was known to be problematic because it decreased the in vivo activity to less than 5% of unmodified interferon-alpha (Osborn et al., *J. Phar. Exp. Ther.* 303(2): 540-548, 2002).

On the other hand, an immunoglobulin (Ig) is composed largely of two regions: Fab having an antigen-binding site and Fc having a complement-binding site. Other attempts were made to fuse a protein drug to an immunoglobulin Fc fragment by genetic recombination. For example, interferon (Korean Pat. Laid-open Publication No. 2003-9464), and interleukin-4 receptor, interleukin-7 receptor or erythropoietin (EPO) receptor (Korean Pat. Registration No. 249572) were previously expressed in mammals in a form fused to an immunoglobulin Fc fragment. International Pat. Publication No. WO 01/03737 describes a fusion protein comprising a cytokine or growth factor linked to an immunoglobulin Fc fragment through an oligopeptide linker.

In addition, U.S. Pat. No. 5,116,964 discloses an LHR (lymphocyte cell surface glycoprotein) or CD4 protein fused to an amino terminus or carboxyl terminus of an immunoglobulin Fc fragment by genetic recombination, and U.S. Pat. No. 5,349,053 describes a fusion protein of IL-2 and an immunoglobulin Fc fragment. Other examples of Fc fusion proteins prepared by genetic recombination include a fusion protein of interferon-beta or a derivative thereof and an immunoglobulin Fc fragment (International Pat. Publication No. WO 00/23472), a fusion protein of IL-5 receptor and an immunoglobulin Fc fragment (U.S. Pat. No. 5,712,121), a fusion protein of interferon-alpha and an Fc fragment of an immunoglobulin G4 (U.S. Pat. No. 5,723,125), and a fusion protein of CD4 protein and an Fc fragment of an immunoglobulin G2 (U.S. Pat. No. 6,451,313). Also, as described in U.S. Pat. No. 5,605,690, an Fc variant having an amino acid alteration especially at a complement-binding site or receptor-binding site can be fused to TNF receptor by recombinant DNA technologies to give a TNFR-IgG1 Fc fusion protein. In this way, methods of preparing an Fc fusion protein using an immunoglobulin Fc fragment modified by genetic recombination are disclosed in U.S. Pat. Nos. 6,277,375, 6,410,008 and 6,444,792.

U.S. Pat. No. 6,660,843 discloses a method of producing a conjugate comprising a target protein fused to an immunoglobulin Fc fragment by means of a linker in *E. coli* by genetic recombination. This method allows the conjugate to be produced at lower cost than when using mammalian expression systems and provides the conjugate in an aglycosylated form. However, since the target protein and the immunoglobulin Fc fragment are produced together in *E. coli*, if the target protein is glycosylated in nature, it is difficult to apply such a target protein using this method. This method has another problem of expressing the conjugate as inclusion bodies, resulting in very high misfolding rates.

However, such Fc fusion proteins produced by genetic recombination have the following disadvantages: protein fusion occurs only in a specific region of an immunoglobulin Fc fragment, which is at an amino- or carboxyl-terminal end; only homodimeric forms and not monomeric forms are produced; and a fusion could take place only between the glycosylated proteins or between the aglycosylated proteins, and it is impossible to make a fusion protein composed of a glycosylated protein and an aglycosylated protein. Further, a new amino acid sequence created by the fusion may trigger immune responses, and a linker region may become susceptible to proteolytic degradation.

On the other hand, with respect to the development of fusion proteins using an immunoglobulin Fc fragment, there is no report of a conjugate comprising a target protein linked to a human-derived native Fc using a crosslinking agent. The preparation of a conjugate using a linker has the advantages of facilitating the selection and control linking sites and orientation of two proteins to be linked together, and allowing the expression in a monomer, dimer or multimer and the preparation of homologous or heterogeneous constructs. The immunoglobulin Fc fragment can be produced by recombinant DNA technologies using mammalian cells or *E. coli*. However, to date, there is no report of a native immunoglobulin Fc fragment that is singly mass-produced with high yields in *E. coli* and applied to long-acting formulations. Also, to date, there has been no attempt for the production of a conjugate comprising a target protein linked to such an *E. coli*-derived immunoglobulin Fc fragment produced by recombinant DNA technologies by means of a crosslinking agent.

On the other hand, immunoglobulins have antibody functions, such as antibody-dependent cell-mediated cytotoxicity (ADCC) or complement-dependent cytotoxicity (CDC), and sugar moieties present at an Fc fragment of immunoglobulins play important roles in the ADCC and CDC effects (Burton D., *Molec. Immun.* 22, 161-206, 1985). Immunoglobulins lacking sugar moieties have serum half-lives similar to glycosylated immunoglobulins but 10 to 1000-fold reduced complement and receptor binding affinities (Waldmann H., *Eur. J. Immunol.* 23, 403-411, 1993; Morrison S., *J. Immunol.* 143, 2595-2601, 1989).

As described above, a variety of methods have been tried for linking a polymer to a physiologically active protein. Conventional methods enhance the stability of polypeptides but remarkably reduce the activity thereof, or improve the activity of the polypeptides regardless of the stability. Thus, there is a need of a method capable of achieving both minimal activity reduction and stability enhancement for a protein drug.

In this regard, leading to the present invention, the intensive and through research into the development of a long-acting protein drug formulation capable of achieving both minimal activity reduction and stability enhancement, which are conventionally considered difficult to accomplish, resulted in the finding that a protein conjugate, prepared by covalent bond an immunoglobulin Fc fragment, a non-peptide polymer and a physiologically active polypeptide, remarkably extends the serum half-life of the physiologically active protein and maintains higher titers than known protein drugs.

DISCLOSURE OF THE INVENTION

It is therefore an object of the present invention to provide a protein conjugate minimizing the activity reduction of a physiologically active polypeptide while extending the serum half-life of the polypeptide, while reducing the risk of inducing immune responses, and a method of preparing such a protein conjugate.

It is another object of the present invention to provide a long-acting protein drug formulation comprising the protein conjugate with the extended serum half-life as an effective component.

It is a further object of the present invention to provide a method of improving the stability and the duration of physiological action by minimizing the activity reduction of a physiologically active polypeptide while enhancing the serum half-life of the polypeptide.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
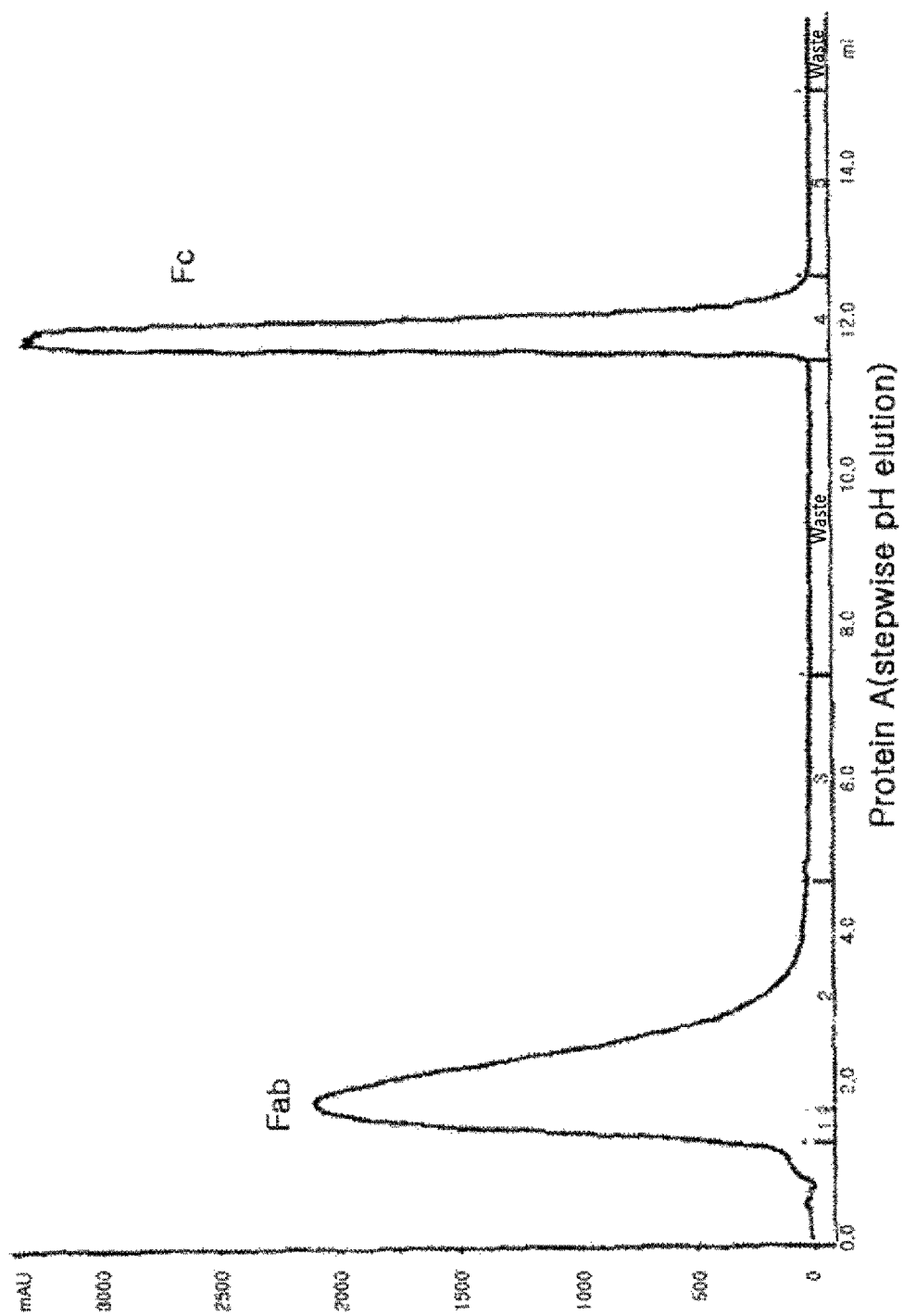
FIG. 1 shows the results of chromatography of an immunoglobulin Fc fragment obtained by cleavage of an immunoglobulin with papain.

In one aspect for accomplishing the above objects, the present invention provides a protein conjugate comprising a physiologically active polypeptide, a non-peptide polymer having a reactive group at both ends and an immunoglobulin Fc fragment, which are covalently linked.

The term "protein conjugate" or "conjugate", as used herein, refers to comprise one or more physiologically active polypeptides, one or more non-peptide polymers having a reactive group at both ends and one or more immunoglobulin Fc fragments, wherein the three components are covalently linked. In addition, to be distinguished from the "conjugate", a construct comprising only two different molecules selected from a physiologically active polypeptide, a non-peptide polymer and an immunoglobulin Fc fragment, wherein the two molecules are covalently linked together, is designated as a "complex".

The protein conjugate of the present invention is a variant of a protein drug made to reduce the physiological activity reduction and to increase the in vivo duration of the protein drug, which is characterized by linking an immunoglobulin Fc fragment to the protein drug.

The immunoglobulin Fc fragment is safe for use as a drug carrier because it is a biodegradable polypeptide that is metabolized in the body. Also, the immunoglobulin Fc fragment has a relatively low molecular weight compared to the whole immunoglobulin molecules, thus being advantageous in the preparation, purification and yield of conjugates due to. Since the immunoglobulin Fc fragment does not contain the Fab fragment, whose amino acid sequence differs among antibody subclasses and which thus is highly non-homogenous, it may greatly increase the homogeneity of substances and be less antigenic.

The term "immunoglobulin Fc fragment", as used herein, refers to a protein that contains the heavy-chain constant region 2 ($C_H2$) and the heavy-chain constant region 3 ($C_H3$) of an immunoglobulin, and not the variable regions of the heavy and light chains, the heavy-chain constant region 1 ($C_H1$) and the light-chain constant region 1 ($C_L1$) of the immunoglobulin. It may further include the hinge region at the heavy-chain constant region. Also, the immunoglobulin Fc fragment of the present invention may contain a portion or all of the heavy-chain constant region 1 ($C_H1$) and/or the light-chain constant region 1 ($C_L1$), except for the variable regions of the heavy and light chains. Also as long as it has a physiological function substantially similar to or better than the native protein the IgG Fc fragment may be a fragment having a deletion in a relatively long portion of the amino acid sequence of $C_H2$ and/or $C_H3$. That is, the immunoglobulin Fc fragment of the present invention may comprise 1) a $C_H1$ domain, a $C_H2$ domain, a $C_H3$ domain and a $C_H4$ domain, 2) a $C_H1$ domain and a $C_H2$ domain, 3) a $C_H1$ domain and a $C_H3$ domain, 4) a $C_H2$ domain and a $C_H3$ domain, 5) a combination of one or more domains and an immunoglobulin hinge region (or a portion of the hinge region), and 6) a dimer of each domain of the heavy-chain constant regions and the light-chain constant region.

The immunoglobulin Fc fragment of the present invention includes a native amino acid sequence and sequence derivatives (mutants) thereof. An amino acid sequence derivative is a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification. Also, other various derivatives are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC site. Techniques of preparing such sequence derivatives of the immunoglobulin Fc fragment are disclosed in International Pat. Publication Nos. WO 97/34631 and WO 96/32478.

Amino acid exchanges in proteins and peptides, which do not generally alter the activity of the proteins, or peptides are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions.

In addition, the Fc fragment, if desired, may be modified by phosphorylation, sulfation, acrylation, glycosylation, methylation, farnesylation, acetylation, amidation, and the like.

The aforementioned Fc derivatives are derivatives that have a biological activity identical to the Fc fragment of the present invention or improved structural stability, for example, against heat, pH, or the like.

In addition, these Fc fragments may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc fragments, and pepsin treatment results in the production of pF'c and F(ab')2 fragments. These fragments may be subjected, for example, to size exclusion chromatography to isolate Fc or pF'c.

Preferably, a human-derived Fc fragment is a recombinant immunoglobulin Fc fragment that is obtained from a microorganism.

In addition, the immunoglobulin Fc fragment of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc fragment results in a sharp decrease in binding affinity to the C1q part of the first complement component C1 and a decrease or loss in antibody-dependent cell-mediated cytotoxicity (ADCC) or complement-dependent cytotoxicity (CDC), thereby not inducing unnecessary immune responses in vivo. In this regard, an immunoglobulin Fc fragment in a deglycosylated or aglycosylated form may be more suitable to the object of the present invention as a drug carrier.

As used herein, the term "deglycosylation" refers to enzymatically remove sugar moieties from an Fc fragment, and the term "aglycosylation" means that an Fc fragment is produced in an unglycosylated form by a prokaryote, preferably *E. coli*.

On the other hand, the immunoglobulin Fc fragment may be derived from humans or other animals including cows, goats, swine, mice, rabbits, hamsters, rats and guinea pigs, and preferably humans. In addition, the immunoglobulin Fc fragment may be an Fc fragment that is derived from IgG, IgA, IgD, IgE and IgM, or that is made by combinations thereof or hybrids thereof. Preferably, it is derived from IgG or IgM, which is among the most abundant proteins in human blood, and most preferably from IgG, which is known to enhance the half-lives of ligand-binding proteins.

On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG1 Fc, IgG2 Fc, IgG3 Fc and IgG4 Fc fragments.

The term "hybrid", as used herein, means that sequences encoding two or more immunoglobulin Fc fragments of different origin are present in a single-chain immunoglobulin Fc fragment. In the present invention, various types of hybrids are possible. That is, domain hybrids may be composed of one to four domains selected from the group consisting of CH1, CH2, CH3 and CH4 of IgG1 Fc, IgG2 Fc, IgG3 Fc and IgG4 Fc, and may include the hinge region.

On the other hand, IgG is divided into IgG1, IgG2, IgG3 and IgG4 subclasses, and the present invention includes combinations and hybrids thereof. Preferred are IgG2 and IgG4 subclasses, and most preferred is the Fc fragment of IgG4 rarely having effector functions such as CDC (complement dependent cytotoxicity) (see, FIGS. 14 and 15).

That is, as the drug carrier of the present invention, the most preferable immunoglobulin Fc fragment is a human IgG4-derived non-glycosylated Fc fragment. The human-derived Fc fragment is more preferable than a non-human derived Fc fragment, which may act as an antigen in the human body and cause undesirable immune responses such as the production of a new antibody against the antigen.

The present invention is characterized in that the immunoglobulin Fc fragment and the protein drug are linked together via a non-peptide polymer.

The term "non-peptide polymer", as used herein, refers to a biocompatible polymer including two or more repeating units linked to each other by a covalent bond excluding the peptide bond.

The non-peptide polymer capable of being used in the present invention may be selected form the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (poly(lactic acid) and PLGA (polylactic-glycolic acid), lipid polymers, chitins, hyaluronic acid, and combinations thereof. Most preferred is poly(ethylene glycol) (PEG). Also, derivatives thereof well known in the art and being easily prepared within the skill of the art are included in the scope of the present invention. The non-peptide polymer preferably ranges from 1 to 100 kDa, and preferably 1 to 20 kDa, in molecular weight. Also, the non-peptide polymer of the present invention, linked to the immunoglobulin Fc fragment, may be one polymer or a combination of different types of polymers.

The non-peptide polymer useful in the present invention has a reactive group capable of binding to the immunoglobulin Fc fragment and the protein drug.

The non-peptide polymer has a reactive group at both ends, which is preferably selected from the group consisting of a reactive aldehyde group, a propione aldehyde group, a butyl aldehyde group, a maleimide group and a succinimide derivative. The succinimide derivative may be succinimidyl propionate, hydroxy succinimidyl, succinimidyl carboxymethyl or succinimidyl carbonate. In particular, when the non-peptide polymer has a reactive aldehyde group at both ends, it is effective in linking at both ends with a physiologically active polypeptide and an immunoglobulin Fc fragment with minimal non-specific reactions. A final product generated by reductive alkylation via an aldehyde bond is much more stable than when linked via an amide bond.

The reactive groups at both ends of the non-peptide polymer may be the same or different. For example, the non-peptide polymer may possess a maleimide group at one end and, at the other end, an aldehyde group, a propionic aldehyde group or a butyl aldehyde group. When a polyethylene glycol (PEG) having a reactive hydroxy group at both ends thereof is used as the non-peptide polymer, the hydroxy group may be activated to various reactive groups by known chemical reactions, or a PEG having a commercially-available modified reactive group may be used so as to prepare the protein conjugate of the present invention.

On the other hand, in the present invention, a complex of the immunoglobulin Fc fragment and the non-peptide polymer is linked to a physiologically active polypeptide to provide a protein conjugate.

The terms "physiologically active polypeptide", "physiologically active protein", "active polypeptide", "polypeptide drug" or "protein drug", as used herein, are interchangeable in their meanings, and are featured in that they are in a physiologically active form exhibiting various in vivo physiological functions.

The protein drug has a disadvantage of being unable to sustain physiological action for a long period of time due to its property of being easily denatured or degraded by proteolytic enzymes present in the body. However, when the polypeptide drug is conjugated to the immunoglobulin Fc fragment of the present invention to form a conjugate, the drug has increased structural stability and degradation half-life. Also, the polypeptide conjugated to the Fc fragment has a much smaller decrease in physiological activity than other known polypeptide drug formulations. Therefore, compared to the in vivo bioavailability of conventional polypeptide drugs, the conjugate of the polypeptide and the immunoglobulin Fc fragment according to the present invention is characterized by having markedly improved in vivo bioavailability. This is also clearly described through embodiments of the present invention. That is, when linked to the immunoglobulin Fc fragment of the present invention, IFNα, G-CSF, hGH and other protein drugs displayed an about two- to six-fold increase in vivo bioavailability compared to their conventional forms conjugated to PEG alone or both PEG and albumin (Tables 8, 9 and 10).

On the other hand, the linkage of a protein and the immunoglobulin Fc fragment of the present invention is featured in that it is not a fusion by a conventional recombination method. A fusion form of the immunoglobulin Fc fragment and an active polypeptide used as a drug by a recombination method is obtained in such a way that the polypeptide is linked to the N-terminus or C-terminus of the Fc fragment, and is thus expressed and folded as a single polypeptide from a nucleotide sequence encoding the fusion form.

This brings about a sharp decrease in the activity of the resulting fusion protein because the activity of a protein as a physiologically functional substance is determined by the conformation of the protein. Thus, when a polypeptide drug is fused with Fc by a recombination method, there is no effect with regard to in vivo bioavailability even when the fusion protein has increased structural stability. Also, since such a fusion protein is often misfolded and thus expressed as inclusion bodies, the fusion method is uneconomical in protein production and isolation yield. Further, when the active form of a polypeptide is in a glycosylated form, the polypeptide should be expressed in eukaryotic cells. In this case, Fc is also glycosylated, and this glycosylation may cause unsuitable immune responses in vivo.

That is, only the present invention makes it possible to produce a conjugate of a glycosylated active polypeptide and an aglycosylated immunoglobulin Fc fragment, and overcomes all of the above problems, including improving protein production yield, because the two components of the complex are individually prepared and isolated by the best systems.

On the other hand, the physiologically active polypeptide applicable to the protein conjugate of the present invention is exemplified by hormones, cytokines, interleukins, interleukin binding proteins, enzymes, antibodies, growth factors, transcription regulatory factors, coagulation factors, vaccines, structural proteins, ligand proteins or receptors, cell surface antigens, receptor antagonists, and derivatives thereof.

In detail, non-limiting examples of the physiologically active polypeptide include human growth hormone, growth hormone releasing hormone, growth hormone releasing peptide, interferons and interferon receptors (e.g., interferon-α, -β and -γ, water-soluble type I interferon receptor, etc.), colony stimulating factors, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29, -30, etc.) and interleukin receptors (e.g., IL-receptor, IL-4 receptor, etc.), enzymes (e.g., glucocerebrosidase, iduronate-2-sulfatase, alpha-galactosidase-A, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin and cytokine binding proteins (e.g., IL-18bp, TNF-binding protein, etc.), macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors (e.g., nerve growth factor, ciliary neurotrophic factor, axogenesis factor-1, glucagon-like peptides (e.g., GLP-1 etc.), brain-natriuretic peptide, glial derived neurotrophic factor, netrin, neurophil inhibitor factor, neurotrophic factor, neuturin, etc.), parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors (e.g., TNFR(P75), TNFR(P55), IL-1 receptor, VEGF receptor, B cell activating factor receptor, etc.), receptor antagonists (e.g., IL1-Ra etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scFv, Fab, Fab', F(ab')2 and Fd), and virus derived vaccine antigens.

In particular, preferred as physiologically active polypeptides are those requiring frequent dosing upon administration to the body for therapy or prevention of diseases, which include human growth hormone, interferons (interferon-α, -β, -γ, etc.), granulocyte colony stimulating factor, erythropoietin (EPO) and antibody fragments. The most preferable polypeptide drug is interferon-alpha. In addition, certain derivatives are included in the scope of the physiologically active polypeptides of the present invention as long as they have function, structure, activity or stability substantially identical to or improved compared over native forms of the physiologically active polypeptides.

In the present invention, an antibody fragment may be Fab, Fab', F(ab')2, Fd or scFv, which is capable of binding to a specific antigen, and preferably Fab'. The Fab fragments contain the variable domain ($V_L$) and const domain ($C_L$) of the light chain and the variable domain ($V_H$) and the first constant domain ($C_H1$) of the heavy chain. The Fab' fragments differ from the Fab fragments in terms of adding several amino acid residues including one or more cysteine residues from the hinge region to the carboxyl terminus of the $C_H1$ domain. The Fd fragments comprise only the $V_H$ and $C_H1$ domain, and the F(ab')2 fragments are produced as a pair of Fab' fragments by either disulfide bonding or a chemical reaction. The scFv (single-chain Fv) fragments comprise the $V_L$ and $V_H$ domains that are linked to each other by a peptide linker and thus are present in a single polypeptide chain.

On the other hand, when an immunoglobulin Fc fragment and a protein drug are linked together by means of a non-peptide polymer, linking sites of the immunoglobulin Fc fragment include one or more free reactive groups of amino acid residues present at the hinge region or constant region. Preferably, the immunoglobulin Fc constant region and the protein drug are covalently linked at an amino terminal end, an amino group of a lysine residue, an amino group of a histidine residue or a free cysteine residue to a reactive group at respective ends of the non-peptide polymer.

The protein conjugate of the present invention may include one or more unit structures of "physiologically active polypeptide-non-peptide polymer-immunoglobulin Fc fragment", wherein all of the components are linearly linked by a covalent bond. Since the non-peptide polymer possesses a reactive group at both ends thereof, it is connected to the physiologically active polypeptide and the immunoglobulin Fc fragment through a covalent bond. That is, to a single immunoglobulin Fc fragment, one or more complexes of a non-peptide polymer with a physiologically active polypeptide may be linked by a covalent bond to provide a monomer, dimer or multimer of the physiologically active polypeptide by means of the immunoglobulin Fc fragment, thereby more effectively achieving improved in vivo activity and stability.

In the protein conjugate of the present invention, the physiologically active protein may be linked to the immunoglobulin Fc fragment at various molar ratios.

In addition, as conventionally known, two different proteins are linked together via an oligopeptide, an amino acid sequence, created at the junction site, has a risk of inducing immune responses, and linking sites of the proteins are limited to an N-terminus and C-terminus. In contrast, since the protein conjugate of the present invention is mediated by a biocompatible non-peptide polymer, it is advantageous in terms of having no side effects such as toxicity or immune response induction and allowing the preparation of various protein conjugates due to its diversity of linking sites.

In addition, the conventional method of directly fusing an immunoglobulin Fc fragment to an active protein by genetic recombination is problematic because it allows the fusion to be made only in a terminal sequence of the immunoglobulin Fc fragment used as a fusion partner and because it limits the yield of the fusion protein due to its production mode being dependent on animal cell culture. The conventional method has further problems in which the activity of the active protein may decrease due to non-native glycosylation, protein folding must accurately occur, and the fusion protein may be produced in a homodimer form. In particular, when conjugates are produced in *E. coli*, insoluble misfolded conjugates are very difficult to remove. In contrast, the protein conjugate of the present invention may achieve a much longer duration of action and a much higher stability while not causing these problems, is preferable with respect to the maintenance of activity of a polypeptide, and allows the preparation of a conjugate comprising a glycosylated therapeutic protein linked to a non-glycosylated Fc.

On the other hand, low molecular weight chemical binders, such as carbodiimide or glutaraldehyde, have the following problems: they bind simultaneously to several sites on a protein, leading to denaturation of the protein, and non-specifically bind, thus making it difficult to control linking sites or to purify a connected protein. In contrast, since the protein conjugate of the present invention employs a non-peptide polymer, it facilitates the control of linking sites, minimizes non-specific reactions and facilitates protein purification.

The usefulness of the present invention is described in more detail based on the embodiments of the present invention, as follows. The protein conjugate (polypeptide-PEG-Fc) of the present invention, comprising a physiologically active polypeptide and an immunoglobulin Fc fragment, which are linked to each end of PEG, exerts much higher stability than a polypeptide-PEG complex or a polypeptide-PEG-albumin conjugate. Pharmacokinetic analysis revealed that IFNα has a serum half-life increased by about 20 times when linked to 40-kDa PEG (IFNα-40K PEG complex) and by about 10 times in an IFNα-PEG-albumin conjugate, compared to the native IFNα. In contrast, an IFNα-PEG-Fc conjugate according to the present invention showed a half-life remarkably increased by about 50 times (see, Table 3). In addition, the same result was observed in other target proteins, human growth hormone (hGH), granulocyte colony-stimulating factor (G-CSF) and its derivative ($^{17}$S-G-CSF), or erythropoietin (EPO). Protein conjugates according to the present invention, each of which comprises a target protein linked to PEG-Fc, displayed increases about 10-fold in mean residence time (MRT) and serum half-life compared to the native forms of the proteins and the forms conjugated to PEG or PEG-albumin (see, Tables 4 to 7).

Figure 12:
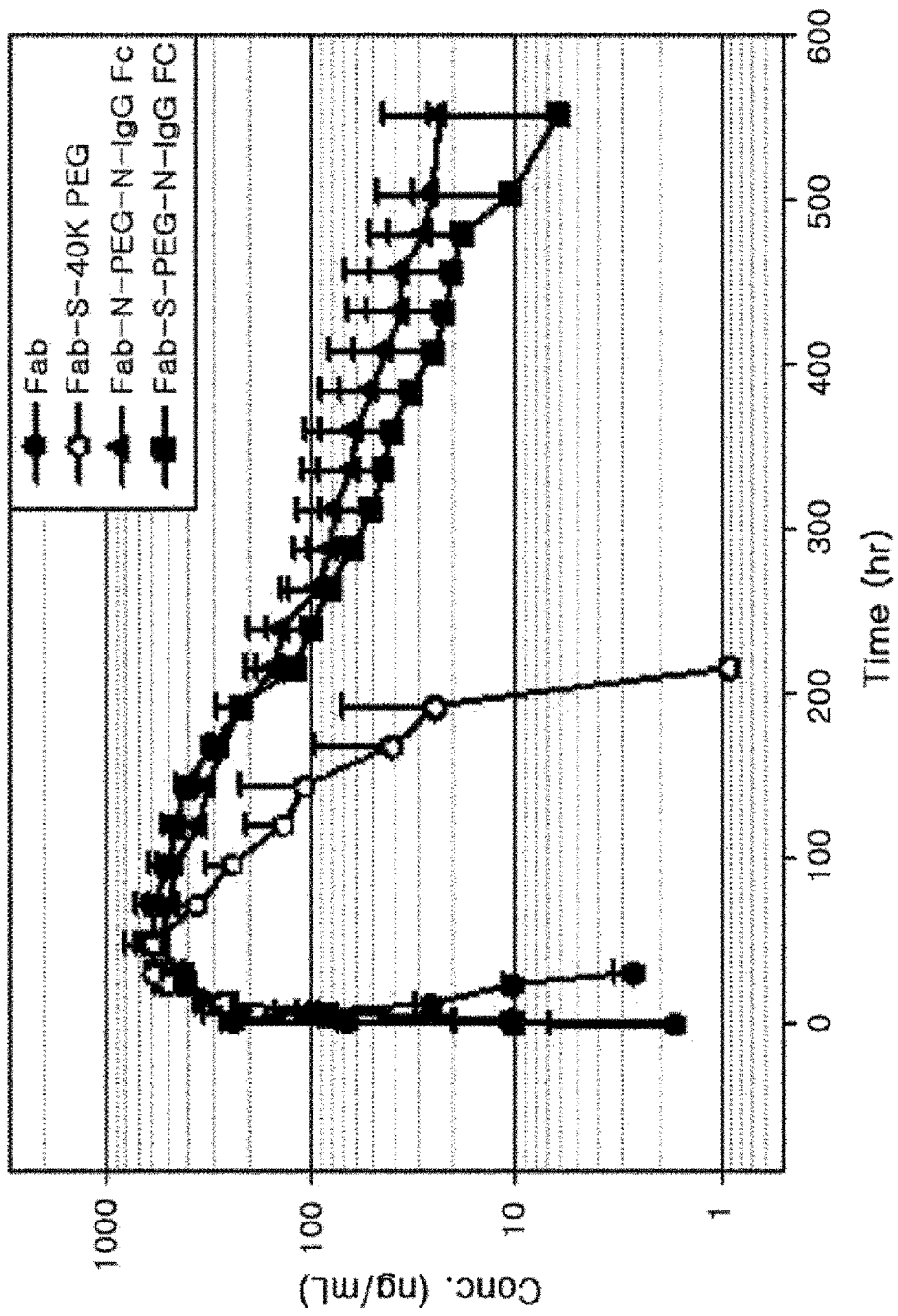
FIG. 12 is a graph showing the pharmacokinetics of a Fab', a Fab'-S-40K PEG complex, a Fab'-N-PEG-N-Fc conjugate and a Fab'-S-PEG-N-Fc conjugate.

In addition, when a PEG-Fc complex is linked to an —SH group near the C-terminus of a Fab' or the N-terminus of the Fab', the resulting Fab'-PEG-Fc conjugate displayed a 2 to 3-fold longer serum half-life than a 40K PEG-Fab' complex (see, FIG. 12).

Figure 8A:
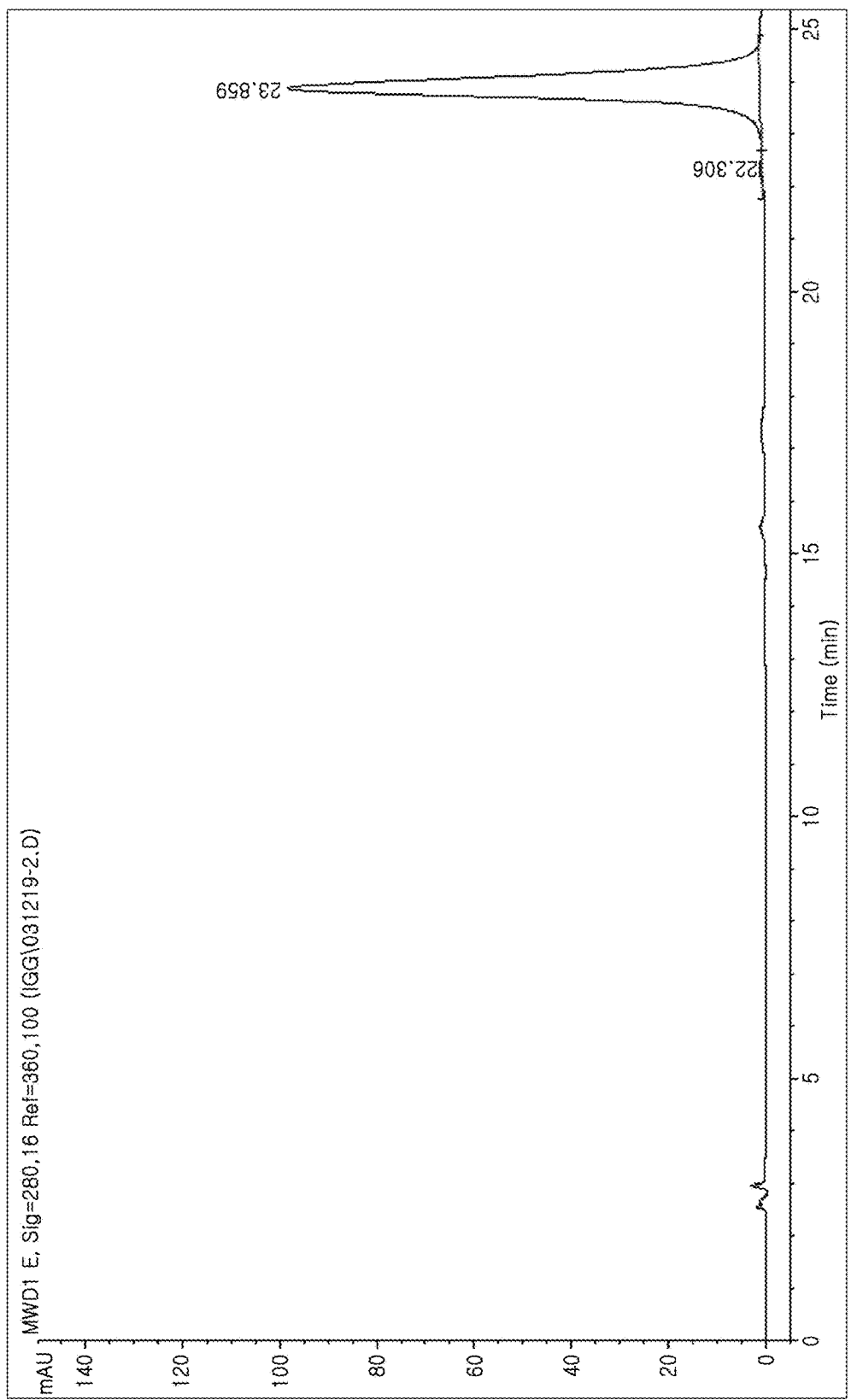
FIGS. 8a to 8c show the results of reverse phase HPLC of IFNα-PEG-Fc, IFNα-PEG-DG Fc and IFNα-PEG-recombinant AG Fc derivative conjugates.
Figure 8B:
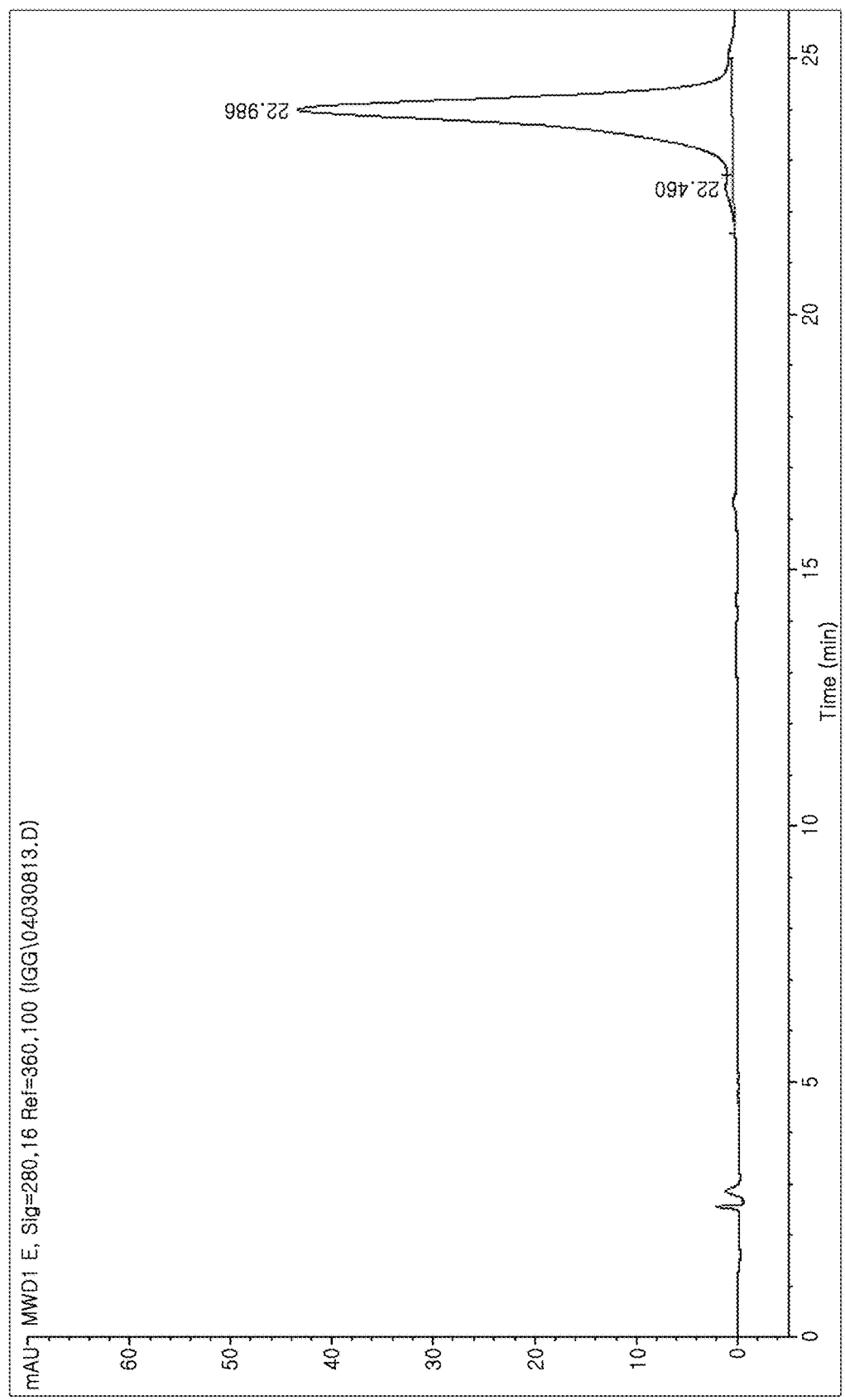
Figure 8C:
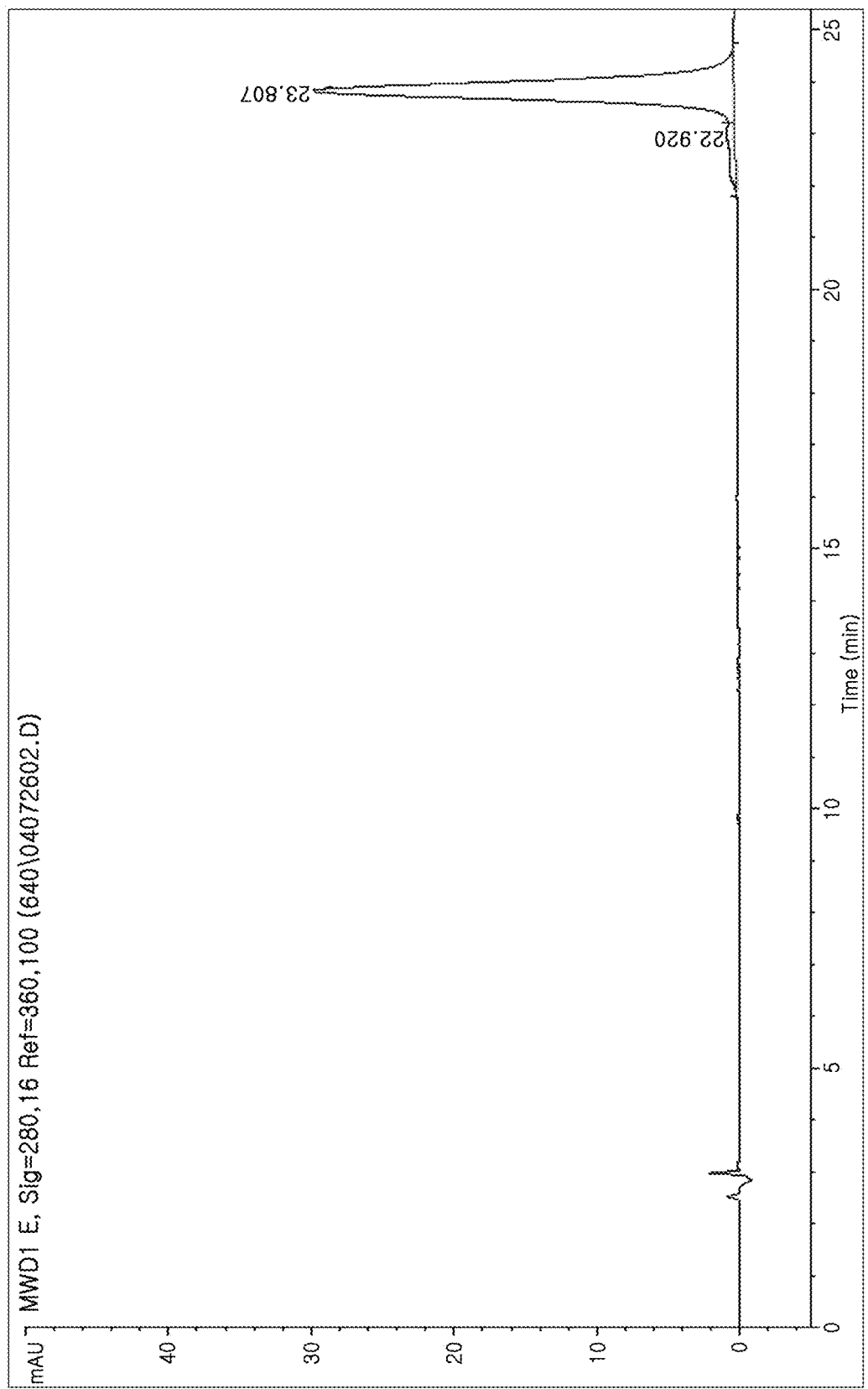
Figure 11:
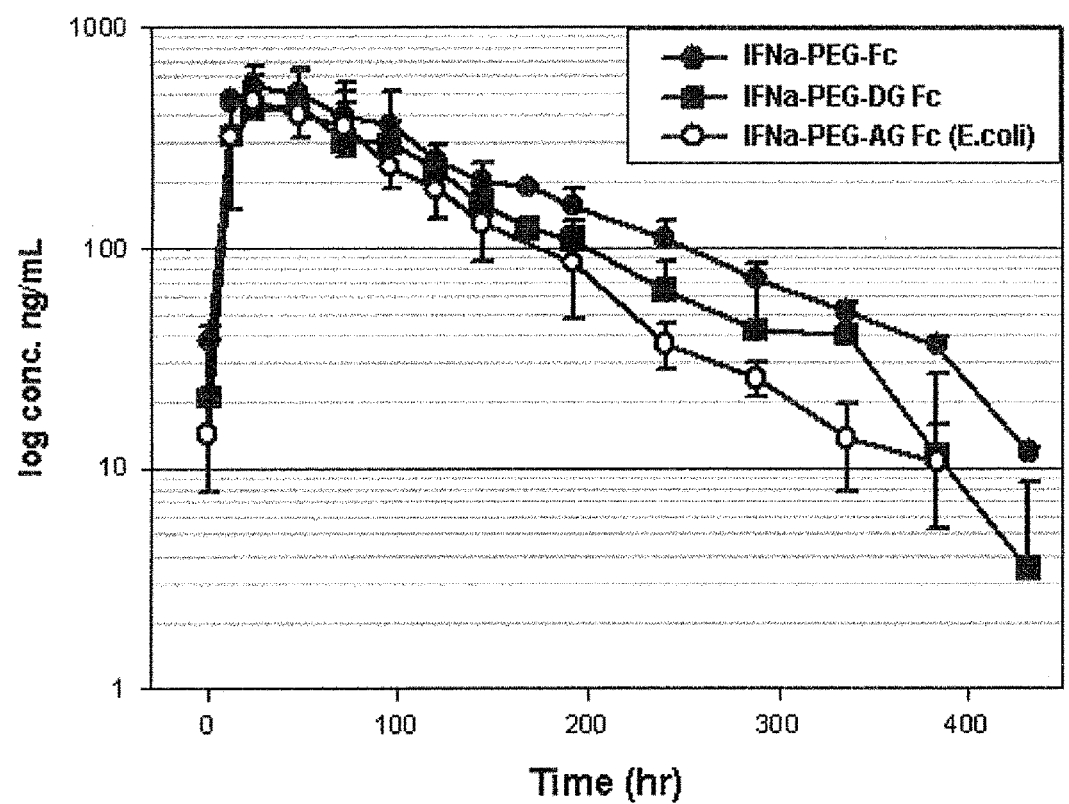
FIG. 11 is a graph showing the results of pharmacokinetic analysis of IFNα-PEG-Fc, IFNα-PEG-DG Fc and IFNα-PEG-recombinant AG Fc derivative conjugates.

Further, when protein conjugates are prepared using deglycosylated immunoglobulin Fc (DG Fc), where sugar moieties are removed, and recombinant aglycosylated immunoglobulin Fc (AG Fc) derivatives, their plasma half-lives and in vitro activity were maintained similar to the protein conjugates prepared using the native Fc (see, Table 3 and FIGS. 8 and 11).

Therefore, since the protein conjugates of the present invention have extended serum half-lives and mean residence time (MRT) when applied to a variety of physiologically active polypeptides including human growth hormone, interferon, erythropoietin, colony stimulating factor or its derivatives, and antibody derivatives, they are useful for developing long-acting formulations of diverse physiologically active polypeptides.

In another aspect, the present invention provides a method of preparing a protein conjugate with improved in vivo duration and stability, comprising: (a) facilitating a reaction between a non-peptide polymer having a reactive group at both ends thereof, a physiologically active polypeptide and an immunoglobulin Fc fragment to be covalently linked; and (b) isolating a resulting conjugate comprising the physiologically active polypeptide and the immunoglobulin Fc fragment which are linked covalently to each end of the non-peptide polymer.

At the step (a), the covalent linkage of the three components occurs sequentially or simultaneously. For example, when the physiologically active polypeptide and the immunoglobulin Fc fragment are linked to each end of the non-peptide polymer, any one of the physiologically active polypeptide and the immunoglobulin Fc fragment is linked to one end of the non-peptide polymer, and the other is then linked to the other end of the non-peptide polymer. This sequential linkage is preferred for minimizing the production of byproducts other than a desired protein conjugate.

Thus, the step (a) may include (a1) covalently linking an immunoglobulin Fc fragment or physiologically active polypeptide to one end of a non-peptide polymer; (a2) isolating a complex comprising the immunoglobulin Fc fragment or the physiologically active polypeptide linked to the non-peptide polymer from the reaction mixture; and (a3) covalently linking a physiologically active polypeptide or immunoglobulin Fc fragment to the other end of the non-peptide polymer of the isolated complex to provide a protein conjugate comprising the immunoglobulin Fc fragment and the physiologically active polypeptide, which are linked to each end of the non-peptide polymer.

At the step (a1), the optimal reaction molar ratio of the physiologically active polypeptide and the non-peptide polymer may range from 1:2.5 to 1:5, and the optimal reaction molar ratio of the immunoglobulin Fc fragment and the non-peptide polymer may range from 1:5 to 1:10.

On the other hand, at the step (a3), the reaction molar ratio of the complex obtained at step (a2) to the immunoglobulin Fc fragment or physiologically active polypeptide may range from 1:0.5 to 1:20, and preferably 1:1 to 1:3.

If desired, the steps (a1) and (a3) may be carried out in the presence of a reducing agent depending on the type of reactive groups at both ends of the non-peptide polymer participating in reactions at the steps (a1) and (a3). Preferred reducing agents may include sodium cyanoborohydride (NaCNBH$_3$), sodium borohydride, dimethylamine borate and pyridine borate.

Taking into consideration purities required at the steps (a2) and (b) and molecular weights and charges of products, a suitable protein isolation method may be selected from methods commonly used for protein isolation in the art. For example, a variety of known methods including size exclusion chromatography and ion exchange chromatography may be applied. If desired, a combination of a plurality of different methods may be used for a high degree of purification.

In a further aspect, the present invention provides a pharmaceutical composition for providing a physiologically active polypeptide having improved in vivo duration and stability, comprising the protein conjugate of the present invention as an effective component along with a pharmaceutically acceptable carrier.

The term "administration", as used herein, means introduction of a predetermined amount of a substance into a patient by a certain suitable method. The conjugate of the present invention may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach. Preferably, the present composition may be administered in an injectable form. In addition, the pharmaceutical composition of the present invention may be administered using a certain apparatus capable of transporting the active ingredients into a target cell.

The pharmaceutical composition comprising the conjugate according to the present invention may include a pharmaceutically acceptable carrier. For oral administration, the pharmaceutically acceptable carrier may include binders, lubricants, disintegrators, excipients, solubilizers, dispersing agents, stabilizers, suspending agents, coloring agents and perfumes. For injectable preparations, the pharmaceutically acceptable carrier may include buffering agents, preserving agents, analgesics, solubilizers, isotonic agents and stabilizers. For preparations for topical administration, the pharmaceutically acceptable carrier may include bases, excipients, lubricants and preserving agents. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into a unit dosage form, such as a multidose container or an ampule as a single-dose dosage form. The pharmaceutical composition may be also formulated into solutions, suspensions, tablets, capsules and long-acting preparations.

On the other hand, examples of carriers, excipients and diluents suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, perfumes, emulsifiers and antiseptics.

A substantial dosage of a drug in combination with the Fc fragment of the present invention as a carrier may be determined by several related factors including the types of diseases to be treated, administration routes, the patient's age, gender, weight and severity of the illness, as well as by the types of the drug as an active component. Since the pharmaceutical composition of the present invention has a very long duration of action in vivo, it has an advantage of greatly reducing administration frequency of pharmaceutical drugs.

A better understanding of the present invention may be obtained through the following examples which are set forth to illustrate, but are not to be construed as the limit of the present invention.

Example 1: Preparation I of
IFNα-PEG-Immunoglobulin Fc Fragment
Conjugate

<Step 1> Preparation of Immunoglobulin Fc Fragment Using Immunoglobulin

Figure 2:
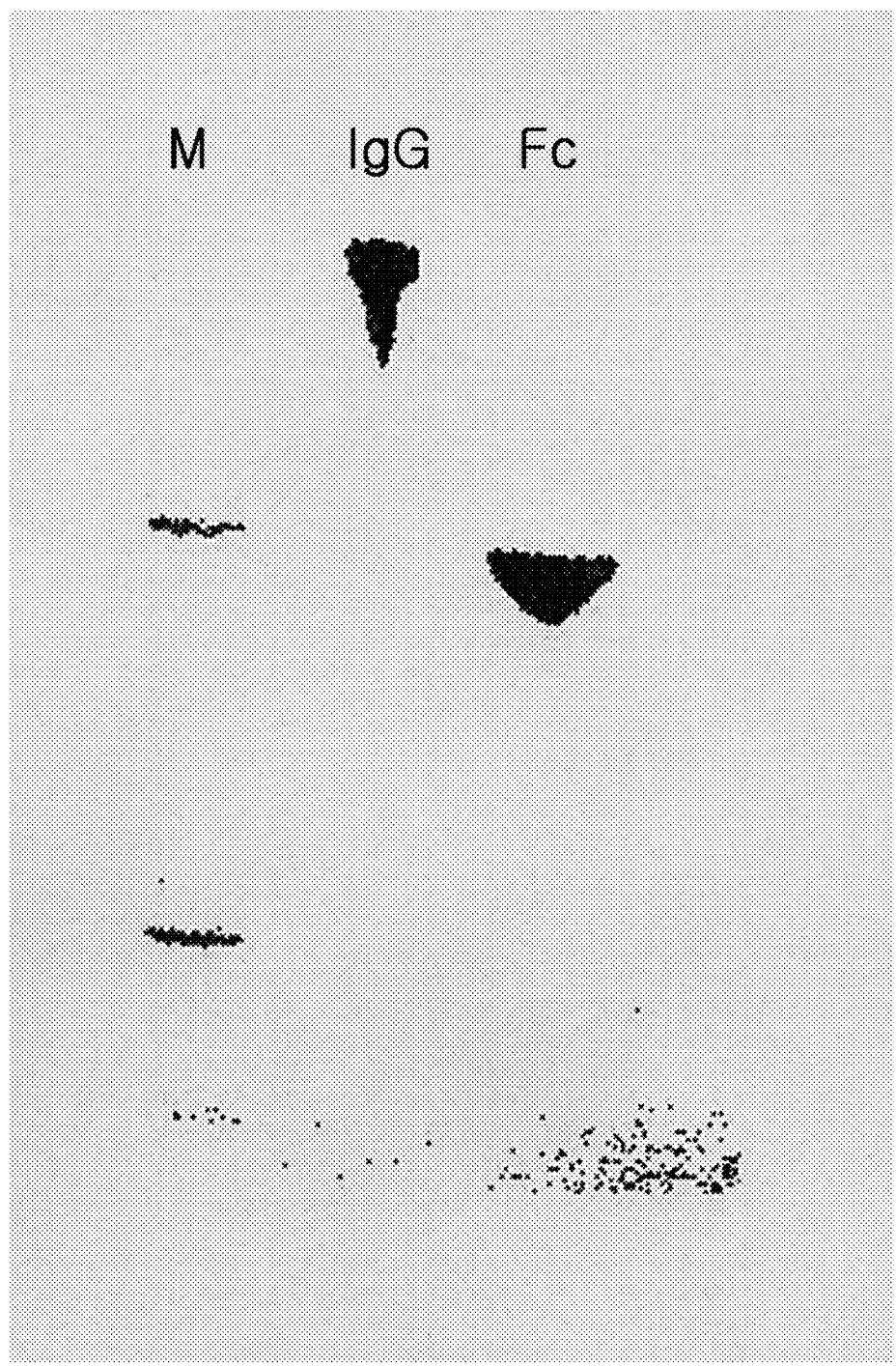
FIG. 2 shows the results of SDS-PAGE of a purified immunoglobulin Fc fragment (M: molecular size marker, lane 1: IgG, lane 2: Fc)

An immunoglobulin Fc fragment was prepared as follows. 200 mg of 150-kDa immunoglobulin G (IgG) (Green Cross, Korea) dissolved in 10 mM phosphate buffer was treated with 2 mg of a proteolytic enzyme, papain (Sigma) at 37° C. for 2 hrs with gentle agitation. After the enzyme reaction, the immunoglobulin Fc fragment regenerated thus was subjected to chromatography for purification using sequentially a Superdex column, a protein A column and a cation exchange column. In detail, the reaction solution was loaded onto a Superdex 200 column (Pharmacia) equilibrated with 10 mM sodium phosphate buffer (PBS, pH 7.3), and the column was eluted with the same buffer at a flow rate of 1 ml/min. Unreacted immunoglobulin molecules (IgG) and F(ab')2, which had a relatively high molecular weight compared to the immunoglobulin Fc fragment, were removed using their property of being eluted earlier than the Ig Fc fragment. Fab fragments having a molecular weight similar to the Ig Fc fragment were eliminated by protein A column chromatography (FIG. 1). The resulting fractions containing the Ig Fc fragment eluted from the Superdex 200 column were loaded at a flow rate of 5 ml/min onto a protein A column (Pharmacia) equilibrated with 20 mM phosphate buffer (pH 7.0), and the column was washed with the same buffer to remove proteins unbound to the column. Then, the protein A column was eluted with 100 mM sodium citrate buffer (pH 3.0) to obtain highly pure immunoglobulin Fc fragment. The Fc fractions collected from the protein A column were finally purified using a cation exchange column (polyCAT, PolyLC Company), wherein this column loaded with the Fc fractions was eluted with a linear gradient of 0.15-0.4 M NaCl in 10 mM acetate buffer (pH 4.5), thus providing highly pure Fc fractions. The highly pure Fc fractions were analyzed by 12% SDS-PAGE (lane 2 in FIG. 2).

<Step 2> Preparation of IFNα-PEG Complex 3.4-kDa polyethylene glycol having an aldehyde reactive group at both ends, ALD-PEG-ALD (Shearwater), was mixed with human interferon alpha-2b (hIFNα-2b, MW: 20 kDa) dissolved in 100 mM phosphate buffer in an amount of 5 mg/ml) at an IFNα:PEG molar ratio of 1:1, 1:2.5, 1:5, 1:10 and 1:20. To this mixture, a reducing agent, sodium cyanoborohydride (NaCNBH$_3$, Sigma), was added at a final concentration of 20 mM and was allowed to react at 4° C. for 3 hrs with gentle agitation to allow PEG to link to the amino terminal end of interferon alpha. To obtain a 1:1 complex of PEG and interferon alpha, the reaction mixture was subjected to size exclusion chromatography using a Superdex$^R$ column (Pharmacia). The IFNα-PEG complex was eluted from the column using 10 mM potassium phosphate buffer (pH 6.0) as an elution buffer, and interferon alpha not linked to PEG, unreacted PEG and dimer byproducts where PEG was linked to two interferon alpha molecules were removed. The purified IFNα-PEG complex was concentrated to 5 mg/ml. Through this experiment, the optimal reaction molar ratio for IFNα to PEG, providing the highest reactivity and generating the smallest amount of byproducts such as dimers, was found to be 1:2.5 to 1:5.

<Step 3> Preparation of IFNα-PEG-Fc Conjugate

To link the IFNα-PEG complex purified in the above step to the N-terminus of an immunoglobulin Fc fragment, the immunoglobulin Fc fragment (about 53 kDa) prepared in the above step 1 was dissolved in 10 mM phosphate buffer and mixed with the IFNα-PEG complex at an IFNα-PEG complex:Fc molar ratio of 1:1, 1:2, 1:4 and 1:8. After the phosphate buffer concentration of the reaction solution was adjusted to 100 mM, a reducing agent, NaCNBH$_3$, was added to the reaction solution at a final concentration of 20 mM and was allowed to react at 4° C. for 20 hrs with gentle agitation. Through this experiment, the optimal reaction molar ratio for IFNα-PEG complex to Fc, providing the highest reactivity and generating the fewest byproducts such as dimers, was found to be 1:2.

<Step 4> Isolation and Purification of the IFNα-PEG-Fc Conjugate

After the reaction of the above step 3, the reaction mixture was subjected to Superdex size exclusion chromatography so as to eliminate unreacted substances and byproducts and purify the IFNα-PEG-Fc protein conjugate produced. After the reaction mixture was concentrated and loaded onto a Superdex column, 10 mM phosphate buffer (pH 7.3) was passed through the column at a flow rate of 2.5 ml/min to remove unbound Fc and unreacted substances, followed by column elution to collect IFNα-PEG-Fc protein conjugate fractions. Since the collected IFNα-PEG-Fc protein conjugate fractions contained a small amount of impurities, unreacted Fc and interferon alpha dimers, cation exchange chromatography was carried out to remove the impurities. The IFNα-PEG-Fc protein conjugate fractions were loaded onto a PolyCAT LP column (PolyLC) equilibrated with 10 mM sodium acetate (pH 4.5), and the column was eluted with a linear gradient of 0-0.5 M NaCl in 10 mM sodium acetate buffer (pH 4.5) using 1 M NaCl. Finally, the IFNα-PEG-Fc protein conjugate was purified using an anion exchange column. The IFNα-PEG-Fc protein conjugate fractions were loaded onto a PolyWAX LP column (PolyLC) equilibrated with 10 mM Tris-HCl (pH 7.5), and the column was then eluted with a linear gradient of 0-0.3 M NaCl in 10 mM Tris-HCl (pH 7.5) using 1 M NaCl, thus isolating the IFNα-PEG-Fc protein conjugate in a highly pure form.

Example 2: Preparation II of IFNα-PEG-Fc Protein Conjugate

<Step 1> Preparation of Fc-PEG Complex 3.4-kDa polyethylene glycol having an aldehyde reactive group at both ends, ALD-PEG-ALD (Shearwater), was mixed with the immunoglobulin Fc fragment prepared in the step 1 of Example 1 at Fc:PEG molar ratios of 1:1, 1:2.5, 1:5, 1:10 and 1:20, wherein the Ig Fc fragment had been dissolved in 100 mM phosphate buffer in an amount of 15 mg/ml. To this mixture, a reducing agent, NaCNBH$_3$ (Sigma), was added at a final concentration of 20 mM and was allowed to react at 4° C. for 3 hrs with gentle agitation. To obtain a 1:1 complex of PEG and Fc, the reaction mixture was subjected to size exclusion chromatography using a Superdex$^R$ column (Pharmacia). The Fc-PEG complex was eluted from the column using 10 mM potassium phosphate buffer (pH 6.0) as an elution buffer, and immunoglobulin Fc fragment not linked to PEG, unreacted PEG and dimer byproducts where PEG was linked to two immunoglobulin Fc fragment molecules were removed. The purified Fc-PEG complex was concentrated to about 15 mg/ml. Through this experiment, the optimal reaction molar ratio for Fc to PEG, providing the highest reactivity and generating the fewest byproducts such as dimers, was found to be 1:3 to 1:10.

<Step 2> Formation and Purification of Conjugate of the Fc-PEG Complex and Interferon Alpha To link the Fc-PEG complex purified in the above step 1 to the N-terminus of IFNα, the Fc-PEG complex was mixed with IFNα dissolved in 10 mM phosphate buffer at Fc-PEG complex: IFNα molar ratios of 1:1, 1:1.5, 1:3 and 1:6. After the phosphate buffer concentration of the reaction solution was adjusted to 100 mM, a reducing agent, NaCNBH$_3$, was added to the reaction solution at a final concentration of 20 mM and was allowed to react at 4° C. for 20 hrs with gentle agitation. After the reaction was completed, unreacted substances and byproducts were removed according to the same purification method as in the step 4 of Example 1, thus isolating the Fc-PEG-IFNα protein conjugate in a highly pure form.

Example 3: Preparation of hGH-PEG-Fc Conjugate

An hGH-PEG-Fc conjugate was prepared and purified according to the same method as in Example 1, except that drug other than interferon alpha, human growth hormone (hGH, MW: 22 kDa) was used and a hGH:PEG molar ratio was 1:5.

Example 4: Preparation of G-CSF-PEG-Fc Conjugate

A G-CSF-PEG-Fc conjugate was prepared and purified according to the same method as in Example 1, except that drug other than interferon alpha, human granulocyte colony stimulating factor (hG-CSF), was used and an hG-CSF:PEG molar ratio was 1:5.

On the other hand, a $^{17}$S-G-CSF-PEG-Fc protein conjugate was prepared and purified according to the same method as described above using a G-CSF derivative, $^{17}$S-G-CSF, having a serine substitution at the seventeenth amino acid residue of the native hG-CSF.

Example 5: Preparation of EPO-PEG-Fc Conjugate

An EPO-PEG-Fc conjugate was prepared and purified according to the same method as in Example 1, except that drug other than interferon alpha, human erythropoietin (EPO), was used and an EPO:PEG molar ratio was 1:5.

Example 6: Preparation of Protein Conjugate Using PEG Having Different Reactive Group An IFNα-PEG-Fc protein conjugate was prepared using PEG having a succinimidyl propionate (SPA) reactive group at both ends, as follows. 3.4-kDa polyethylene glycol, SPA-PEG-SPA (Shearwater), was mixed with 10 mg of interferon alpha dissolved in 100 mM phosphate buffer at IFNα:PEG molar ratios of 1:1, 1:2.5, 1:5, 1:10 and 1:20. The mixture was then allowed to react at room temperature with gentle agitation for 2 hrs. To obtain a 1:1 complex of PEG and interferon alpha (IFNα-PEG complex), where PEG was linked selectively to the amino group of a lysine residue of interferon alpha, the reaction mixture was subjected to Superdex size exclusion chromatography. The IFNα-PEG complex was eluted from the column using 10 mM potassium phosphate buffer (pH 6.0) as an elution buffer, and interferon alpha not linked to PEG, unreacted PEG and dimer byproducts in which two interferon alpha molecules were linked to both ends of PEG were removed. To link the IFNα-PEG complex to the amino group of a lysine residue of immunoglobulin Fc, the purified IFNα-PEG complex was concentrated to about 5 mg/ml, and an IFNα-PEG-Fc conjugate was prepared and purified according to the same methods as in the steps 3 and 4 of Example 1. Through this experiment, the optimal reaction molar ratio for IFNα to PEG, providing the highest reactivity and generating the fewest byproducts such as dimers, was found to be 1:2.5 to 1:5.

On the other hand, another IFNα-PEG-Fc conjugate was prepared according to the same methods as described above using PEG) having an N-hydroxysuccinimidyl (NHS) reactive group at both ends, NHS-PEG-NHS (Shearwater), or PEG having a buthyl aldehyde reactive group at both ends, BUA-PEG-BUA (Shearwater).

Example 7: Preparation of Protein Conjugate Using PEG Having Different Molecular Weight An IFNα-10K PEG complex was prepared using 10-kDa polyethylene glycol having an aldehyde reactive group at both ends, ALD-PEG-ALD (Shearwater). This complex was prepared and purified according to the same method as in the step 2 of Example 1. Through this experiment, the optimal reaction molar ratio for IFNα to 10-kDa PEG, providing the highest reactivity and generating the fewest byproducts such as dimers, was found to be 1:2.5 to 1:5. The purified IFNα-10K PEG complex was concentrated to about 5 mg/ml, and, using this concentrate, an IFNα-10K PEG-Fc conjugate was prepared and purified according to the same methods as in the steps 3 and 4 of Example 1.

Example 8: Preparation of Fab'-S-PEG-N-Fc Conjugate (—SH Group)

<Step 1> Expression and Purification of Fab'

An *E. coli* transformant, BL21/poDLHF (accession number: KCCM-10511), expressing anti-tumor necrosis factor-alpha Fab', was grown in 100 ml of LB medium overnight with agitation, and was inoculated in a 5-L fermentor (Marubishi) and cultured at 30° C. and 500 rpm and at an air flow rate of 20 vvm. To compensate for the insufficient nutrients for bacterial growth during fermentation, the cultures were supplemented with glucose and yeast extracts according to the fermented states of bacteria. When the cultures reached an $OD_{600}$ value of 80-100, an inducer, IPTG, was added to the cultures to induce protein expression. The cultures were further cultured for 40 to 45 hrs until the OD value at 600 nm increased to 120 to 140. The fermentation fluid thus obtained was centrifuged at 20,000×g for 30 min. The supernatant was collected, and the pellet was discarded.

The supernatant was subjected to the following three-step column chromatography to purify anti-tumor necrosis factor-alpha Fab'. The supernatant was loaded onto a HiTrap protein G column (5 ml, Pharmacia) equilibrated with 20 mM phosphate buffer (pH 7.0), and the column was eluted with 100 mM glycine (pH 3.0). The collected Fab' fractions were then loaded onto a Superdex 200 column (Pharmacia) equilibrated with 10 mM sodium phosphate buffer (PBS, pH 7.3), and this column was eluted with the same buffer. Finally, the second Fab' fractions were loaded onto a polyCAT 21×250 column (PolyLC), and this column was eluted with a linear NaCl gradient of 0.15-0.4 M in 10 mM acetate buffer (pH 4.5), thus providing highly pure anti-tumor necrosis factor-alpha Fab' fractions.

<Step 2> Preparation and Purification of Fc-PEG Complex

To link a PEG linker to the N-terminus of an immunoglobulin Fc, the immunoglobulin Fc prepared according to the same method as in the step 1 of Example 1 was dissolved in 100 mM phosphate buffer (pH 6.0) at a concentration of 5 mg/ml, and was mixed with NHS-PEG-MAL (3.4 kDa, Shearwater) at an Fc:PEG molar ratio of 1:10, followed by incubation at 4° C. for 12 hrs with gentle agitation.

After the reaction was completed, the reaction buffer was exchanged with 20 mM sodium phosphate buffer (pH 6.0) to remove unbound NHS-PEG-MAL. Then, the reaction mixture was loaded onto a polyCAT column (PolyLC). The column was eluted with a linear NaCl gradient of 0.15-0.5 M in 20 mM sodium phosphate buffer (pH 6.0). During this elution, the immunoglobulin Fc-PEG complex was eluted earlier than unreacted immunoglobulin Fc, and the unreacted Ig Fc was eluted later, thereby eliminating the unreacted Ig Fc molecules.

<Step 3> Preparation and Purification of Fab'-S-PEG-N-Fc Conjugate (—SH Group)

To link the immunoglobulin Fc-PEG complex to a cysteine group of the Fab', the Fab' purified in the above step 1 was dissolved in 100 mM sodium phosphate buffer (pH 7.3) at a concentration of 2 mg/ml, and was mixed with the immunoglobulin Fc-PEG complex prepared in the above step 2 at a Fab':complex molar ratio of 1:5. The reaction mixture was concentrated to a final protein concentration of 50 mg/ml and incubated at 4° C. for 24 hrs with gentle agitation.

After the reaction was completed, the reaction mixture was loaded onto a Superdex 200 column (Pharmacia) equilibrated with 10 mM sodium phosphate buffer (pH 7.3), and the column was eluted with the same buffer at a flow rate of 1 ml/min. The coupled Fab'-S-PEG-N-Fc conjugate was eluted relatively earlier due to its high molecular weight, and unreacted immunoglobulin Fc-PEG complex and Fab' were eluted later, thereby eliminating the unreacted molecules. To completely eliminate unreacted immunoglobulin Fc-PEG, the collected Fab'-S-PEG-N-Fc conjugate fractions were again loaded onto a polyCAT 21×250 column (PolyLC), and this column was eluted with a linear NaCl gradient of 0.15-0.5 M in 20 mM sodium phosphate buffer (pH 6.0), thus providing a pure Fab'-S-PEG-N-Fc conjugate comprising the Fc-PEG complex linked to an —SH group near the C-terminus of the Fab'.

Example 9: Preparation of Fab'-N-PEG-N-Fc Conjugate (N-Terminus)

<Step 1> Preparation and Purification of Fab'-PEG Complex (N-Terminus)

40 mg of the Fab' purified in the step 1 of Example 8 was dissolved in 100 mM sodium phosphate buffer (pH 6.0) at a concentration of 5 mg/ml, and was mixed with butyl ALD-PEG-butylALD (3.4 kDa, Nektar) at a Fab':PEG molar ratio of 1:5. A reducing agent, NaCNBH$_3$, was added to the reaction mixture at a final concentration of 20 mM, and the reaction mixture was then allowed to react at 4° C. for 2 hrs with gentle agitation.

After the reaction was completed, the reaction buffer was exchanged with 20 mM sodium phosphate buffer (pH 6.0). Then, the reaction mixture was loaded onto a polyCAT column (PolyLC). The column was eluted with a linear NaCl gradient of 0.15-0.4 M in 20 mM acetate buffer (pH 4.5). During this column elution, the Fab'-PEG complex comprising the PEG linker lined to the N-terminus of the Fab' was eluted earlier than unreacted Fab', and the unreacted Fab' was eluted later, thereby eliminating the unreacted Fab' molecules.

<Step 2> Preparation and Purification of Fab'-N-PEG-N-Fc Conjugate

To link the Fab'-PEG complex purified in the above step 1 to the N-terminus of an immunoglobulin Fc, the Fab'-PEG complex was dissolved in 100 mM sodium phosphate buffer (pH 6.0) at a concentration of 10 mg/ml, and was mixed with the immunoglobulin Fc dissolved in the same buffer at a Fab'-PEG complex:Fc molar ratio of 1:5. After the reaction mixture was concentrated to a final protein concentration of 50 mg/ml, a reducing agent, NaCNBH$_3$, was added to the reaction mixture at a final concentration of 20 mM, and the reaction mixture was then reacted at 4° C. for 24 hrs with gentle agitation.

After the reaction was completed, the reaction mixture was loaded onto a Superdex 200 column (Pharmacia) equilibrated with 10 mM sodium phosphate buffer (pH 7.3), and the column was eluted with the same buffer at a flow rate of 1 ml/min. The coupled Fab'-N-PEG-N-Fc conjugate was eluted relatively earlier due to its high molecular weight, and unreacted immunoglobulin Fc and Fab'-PEG complex were eluted later, thereby eliminating the unreacted molecules. To completely eliminate the unreacted immunoglobulin Fc molecules, the collected Fab'-N-PEG-N-Fc conjugate fractions were again loaded onto a polyCAT 21×250 column (PolyLC), and this column was eluted with a linear NaCl gradient of 0.15-0.5 M in 20 mM sodium phosphate buffer (pH 6.0), thus providing a pure Fab'-N-PEG-N-Fc conjugate comprising the immunoglobulin Fc-PEG complex linked to the N-terminus of the Fab'.

Example 10: Preparation and Purification of Deglycosylated Immunoglobulin Fc 200 mg of an immunoglobulin Fc prepared according to the same method as in Example 1 was dissolved in 100 mM phosphate buffer (pH 7.5) at a concentration of 2 mg/ml, and was mixed with 300 U/mg of a deglycosylase, PNGase F (NEB). The reaction mixture was allowed to react at 37° C. for 24 hrs with gentle agitation. Then, to purify the deglycosylated immunoglobulin Fc, the reaction mixture was loaded onto a SP Sepharose FF column (Pharmacia), and the column was eluted with a linear NaCl gradient of 0.1-0.6 M in 10 mM acetate buffer (pH 4.5) using 1 M NaCl. The native immunoglobulin Fc was eluted earlier, and the deglycosylated immunoglobulin Fc (DG Fc) was eluted later.

Example 11: Preparation of IFNα-PEG-DG Fc Conjugate

To link the deglycosylated immunoglobulin Fc prepared in Example 10 to the IFNα-PEG complex purified in the step 2 of Example 1, the IFNα-PEG complex was mixed with the DG Fc dissolved in 10 mM phosphate buffer at IFNα-PEG complex: DG Fc molar ratios of 1:1, 1:2, 1:4 and 1:8. After the phosphate buffer concentration of the reaction solution was adjusted to 100 mM, a reducing agent, NaCNBH$_3$, was added to the reaction solution at a final concentration of 20 mM and was allowed to react at 4° C. for 20 hrs with gentle agitation. Through this experiment, the optimal reaction molar ratio for IFNα-PEG complex to DG Fc, providing the highest reactivity and generating the fewest byproducts such as dimers, was found to be 1:2.

After the coupling reaction, the reaction mixture was subjected to size exclusion chromatography using a SuperdexR column (Pharmacia) so as to eliminate unreacted substances and byproducts and purify the IFNα-PEG-DG Fc protein conjugate. After the reaction mixture was loaded onto the column, a phosphate buffer (pH 7.3) was passed through the column at a flow rate of 2.5 ml/min to remove unbound DG Fc and unreacted substances, followed by column elution to collect IFNα-PEG-DG Fc protein conjugate fractions. Since the collected IFNα-PEG-DG Fc protein conjugate fractions contained a small amount of impurities, unreacted DG Fc and IFNα-PEG complex, cation exchange chromatography was carried out to remove the impurities. The IFNα-PEG-DG Fc protein conjugate fractions were loaded onto a PolyCAT LP column (PolyLC) equilibrated with 10 mM sodium acetate (pH 4.5), and the column was eluted with a linear gradient of 0-0.6 M NaCl in 10 mM sodium acetate buffer (pH 4.5) using 1 M NaCl. Finally, the IFNα-PEG-DG Fc protein conjugate was purified using an anion exchange column. The IFNα-PEG-Fc protein conjugate fractions were loaded onto a PolyWAX LP column (PolyLC) equilibrated with 10 mM Tris-HCl (pH 7.5), and the column was then eluted with a linear gradient of 0-0.3 M NaCl in 10 mM Tris-HCl (pH 7.5) using 1 M NaCl, thus isolating the IFNα-PEG-DG Fc protein conjugate in a highly pure form.

Example 12: Preparation and Purification of Recombinant Aglycosylated Immunoglobulin Fc Derivative <Preparation of IgG4 Fc Derivative 1 Expression Vector>

To prepare human immunoglobulin IgG4 heavy chain constant regions, a first derivative (IgG4 delta-Cys), having a nine amino acid deletion at the amino terminus of the native hinge region, and a second derivative (IgG4 monomer), lacking the hinge region by a deletion of all of twelve amino acids of the hinge region, were prepared. As an expression vector containing an E. coli secretory sequence, pT14S1SH-4T20V22Q (Korean Pat. No. 38061), developed prior to the present invention by the present invention, was used.

To obtain human immunoglobulin IgG4 heavy chain constant regions, RT-PCR was carried out using RNA isolated from human blood cells as a template, as follows. First, total RNA was isolated from about 6 ml of blood using a Qiamp RNA blood kit (Qiagen), and gene amplification was performed using the total RNA as a template and a One-Step RT-PCR kit (Qiagen). In this PCR, a pair of synthesized primers represented by SEQ ID Nos. 1 and 2 and another pair of synthesized primers represented by SEQ ID Nos. 2 and 3 were used. SEQ ID NO. 1 is a nucleotide sequence starting from the 10th residue, serine, of 12 amino acid residues, below, of the hinge region of IgG4 (SEQ ID NO: 7). SEQ ID NO. 3 was designed to have a nucleotide sequence encoding a $C_H2$ domain having alanine as a first amino acid residue. SEQ ID NO. 2 was designed to have a BamHI recognition site containing a stop codon.

```
1    2    3    4    5    6    7    8    9    10   11   12
                                                   (SEQ ID NO: 7)
gag  tcc  aaa  tat  ggt  ccc  cca  tgc  cca  tca  tgc  cca (SEQ ID NO: 8)
Glu  Ser  Lys  Tyr  Gly  Pro  Pro  Cys  Pro  Ser  Cys  Pro
```

To clone each of the amplified IgG4 constant region fragments into an expression vector containing an E. coli secretory sequence derivative, the pT14S1SH-4T20V22Q (Korean Pat. No. 38061) developed prior to the present invention by the present inventors was used. This expression vector contains a heat-stable enterotoxin secretory sequence derivative that has a nucleotide sequence represented by SEQ ID NO. 4. To facilitate cloning, a StuI recognition site was inserted into an end of the E. coli heat-stable enterotoxin secretory sequence derivative of the pT14S1SH-4T20V22Q plasmid through site-directed mutagenesis using a pair of primers represented by SEQ ID Nos. 5 and 6 to induce mutagenesis to introduce the StuI site at a nucleotide sequence coding for the last amino acid residue of the secretory sequence. This insertion of the StuI site was found to be successful by DNA sequencing. The resulting pT14S1SH-4T20V22Q plasmid containing a StuI site was designated as "pmSTII". The pmSTII plasmid was treated with StuI and BamHI and subjected to agarose gel electrophoresis, and a large fragment (4.7 kb), which contained the E. coli heat-stable enterotoxin secretory sequence derivative, was purified. Then, the amplified gene fragments were digested with BamHI and ligated with the linearized expression vector, thus providing pSTIIdCG4Fc and pSTIIG4Mo.

The final expression vectors were individually transformed into E. coli BL21(DE3), and the resulting transformants were designated as "BL21/pSTIIdCG4Fc (HM10932)" and "BL21/pSTIIdCG4Mo (HM10933)", which were deposited at the Korean Culture Center of Microorganisms (KCCM) on Sep. 15, 2004 and assigned accession numbers KCCM-10597 and KCCM-10598, respectively. Thereafter, when the cultures reached an $OD_{600}$ value of 80, an inducer, IPTG, was added to the cultures to induce protein expression. The cultures were further cultured for 40 to 45 hrs until the OD value at 600 nm increased to 100 to 120. The E. coli cells collected from the fermentation fluids were disrupted, and the resulting cell lysates were subjected to two-step column chromatography to purify the recombinant immunoglobulin constant region derivatives present in the cytosol of E. coli.

5 ml of a protein-A affinity column (Pharmacia) was equilibrated with PBS, and the cell lysates were loaded onto the column at a flow rate of 5 ml/min. Unbound proteins were washed out with PBS, and bound proteins were eluted with 100 mM citrate (pH 3.0). The collected fractions were desalted using a HiPrep 26/10 desalting column (Pharmacia) with 10 mM Tris buffer (pH 8.0). Then, secondary anion exchange column chromatography was carried out using 50 ml of a Q HP 26/10 column (Pharmacia). The primary purified recombinant aglycosylated immunoglobulin Fc fractions were loaded onto the Q-Sepharose HP 26/10 column, and the column was eluted with a linear gradient of 0-0.2 M NaCl in 10 mM Tris buffer (pH 8.0), thus providing a highly pure recombinant aglycosylated immunoglobulin Fc (AG Fc) derivative, IgG4 delta-Cys and a highly pure IgG4 monomer fraction.

Example 13: Preparation of Conjugate of IFNα-PEG Complex and Recombinant AG Fc Derivative According to the same methods as in Examples 1 and 11, the IFNα-PEG complex was linked to the N terminus of the IgG4 delta-Cys as an AG Fc derivative prepared in Example 12. After the coupling reaction, unreacted substances and byproducts were removed from the reaction mixture, and the thus-produced IFNα-PEG-AG Fc protein conjugate (I) was primarily purified using 50 ml of a Q HP 26/10 column (Pharmacia) and further purified by a high-pressure liquid chromatographic assay using a polyCAT 21.5×250 column (polyLC), thus purifying the conjugate to a high degree. The coupling reaction solution was desalted using a HiPrep 26/10 desalting column (Pharmacia) with 10 mM Tris buffer (pH 8.0). Then, the reaction solution was then loaded onto 50 ml of a Q HP 26/10 column (Pharmacia) at a flow rate of 8 ml/min, and this column was eluted with a linear NaCl gradient of 0-0.2 M to obtain desired fractions. The collected fractions were again loaded onto a polyCAT 21.5×250 column equilibrated with 10 mM acetate buffer (pH 5.2) at a flow rate of 15 ml/min, and this column was eluted with a linear NaCl gradient of 0.1-0.3 M, thus providing highly pure fractions. According to the same method as described above, another IFNα-PEG-AG Fc protein conjugate (II) was prepared using another AG Fc derivative prepared in Example 12, IgG4 monomer.

Example 14: Preparation of EPO-PEG-Recombinant AG Fc Derivative Conjugate

According to the same method as in Example 13, an EPO-PEG-recombinant AG Fc derivative conjugate was prepared by linking an AG Fc derivative, IgG4 delta-Cys, to the EPO-PEG complex.

Comparative Example 1: Preparation of IFNα-40K PEG Complex 5 mg of interferon alpha was dissolved in 100 mM phosphate buffer to obtain a final volume of 5 ml, and was mixed with 40-kDa activated methoxy-PEG-aldehyde (Shearwater), at an IFNα:40-kDa PEG molar ratio of 1:4. To this mixture, a reducing agent, NaCNBH$_3$ was added at a final concentration of 20 mM and was allowed to react at 4° C. for 18 hrs with gentle agitation. To inactivate PEG, which did not react with IFNα, Ethanolamine was added to the reaction mixture at a final concentration of 50 mM.

A Sephadex G-25 column (Pharmacia) was used to remove unreacted PEG and exchange the buffer with another buffer. First, this column was equilibrated with two column volumes (CV) of 10 mM Tris-HCl buffer (pH 7.5), and was loaded with the reaction mixture. Flow throughs were detected by measuring the absorbance at 260 nm using a UV spectrophotometer. When the column was eluted with the same buffer, interferon alpha modified by adding PEG having a higher molecular weight to its N-terminus was eluted earlier, and unreacted PEG was eluted later, thus allowing isolation of only IFNα-40K PEG.

The following chromatography was carried out to further purify the IFNα-40K PEG complex from the collected fractions. 3 ml of a PolyWAX LP column (PolyLC) was equilibrated with 10 mM Tris-HCl (pH 7.5). The collected fractions containing the IFNα-40K PEG complex was loaded onto the column at a flow rate of 1 ml/min, and the column was washed with 15 ml of the equilibrium buffer. Then, the column was eluted with a linear NaCl gradient of 0-100% using 30 ml of 1 M NaCl, thus eluting interferon alpha conjugated to tri-, di- and mono-PEG, sequentially. To further purify the mono-PEG-conjugated interferon alpha, the collected fractions containing the mono-PEG-conjugated interferon alpha were subjected to size exclusion chromatography. The fractions were concentrated and loaded onto a Superdex 200 column (Pharmacia) equilibrated with 10 mM sodium phosphate buffer (pH 7.0), and the column was eluted with the same buffer at a flow rate of ml/min. The tri- and di-PEG-conjugated interferon alpha molecules were removed based on their property of being eluted earlier than the mono-PEG-conjugated interferon alpha, thus isolating the mono-PEG-conjugated interferon alpha in a highly pure form.

According to the same method as described above, 40-kDa PEG was conjugated to the N-terminus of human growth hormone, granulocyte colony stimulating factor (G-CSF), and a derivative of G-CSF, thus providing hGH-40K PEG, G-CSF-40K PEG and 40K PEG-$^{17}$S-G-CSF derivative complexes.

Comparative Example 2: Preparation of IFNα-PEG-Albumin Conjugate

To link the IFNα-PEG complex purified in the step 2 of Example 1 to the N-terminus of albumin, the IFNα-PEG complex was mixed with human serum albumin (HSA, about 67 kDa, Green Cross) dissolved in 10 mM phosphate buffer at an IFNα-PEG complex:albumin molar ratio of 1:1, 1:2, 1:4 and 1:8. After the phosphate buffer concentration of the reaction solution was adjusted to 100 mM, a reducing agent, NaCNBH$_3$, was added to the reaction solution at a final concentration of 20 mM and was allowed to react at 4° C. for 20 hrs with gentle agitation. Through this experiment, the optimal reaction molar ratio for IFNα-PEG complex to albumin, providing the highest reactivity and generating the fewest byproducts such as dimers, was found to be 1:2.

After the coupling reaction, the reaction mixture was subjected to size exclusion chromatography using a SuperdexR column (Pharmacia) so as to eliminate unreacted substances and byproducts and purify the IFNα-PEG-albumin protein conjugate produced. After the reaction mixture was concentrated and loaded onto the column, 10 mM sodium acetate buffer passed through the column at a flow rate of 2.5 ml/min to remove unbound albumin and unreacted substances, followed by column elution to purify only IFNα-PEG-albumin protein conjugate. Since the collected IFNα-PEG-albumin protein conjugate fractions contained a small amount of impurities, unreacted albumin and interferon alpha dimers, cation exchange chromatography was carried out to remove the impurities. The IFNα-PEG-albumin protein conjugate fractions were loaded onto a SP5PW column (Waters) equilibrated with 10 mM sodium acetate (pH 4.5), and the column was eluted with a linear gradient of 0-0.5 M NaCl in 10 mM sodium acetate buffer (pH 4.5) using 1 M NaCl, thus isolating the IFNα-PEG-albumin protein conjugate in a highly pure form.

According to the same method as described above, albumin was conjugated to human growth hormone, G-CSF, and a derivative of G-CSF, thus providing hGH-PEG-albumin, G-CSF-PEG-albumin and $^{17}$S-G-CSF-PEG-albumin conjugates.

Comparative Example 3: Preparation of Fab'-S-40K PEG Complex

The free cysteine residue of the Fab' purified in the step 1 of Example 8 was activated by incubation in an activation buffer (20 mM sodium acetate (pH 4.0), 0.2 mM DTT) for 1 hr. After the buffer was exchanged by a PEG modification buffer, 50 mM potassium phosphate (pH 6.5), maleimide-PEG (MW: 40 kDa, Shearwater) was added thereto at a Fab':40-kDa PEG molar ratio of 1:10 and was reacted to react at 4° C. for 24 hrs with gentle agitation.

After the reaction was completed, the reaction solution was loaded onto a Superdex 200 column (Pharmacia) equilibrated with 10 mM sodium phosphate buffer (pH 7.3), and the column was eluted with the same buffer at a flow rate of 1 ml/min. The Fab' conjugated 40-kDa PEG (Fab'-40K PEG) was eluted relatively earlier due to its high molecular weight, and unreacted Fab' was eluted later, thereby eliminating the unreacted Fab'. To completely eliminate the unreacted Fab', the collected Fab'-40K PEG complex fractions were again loaded onto a polyCAT 21×250 column (PolyLC), and this column was eluted with a linear NaCl gradient of 0.15-0.5 M in 20 mM sodium phosphate buffer (pH 4.5), thus providing a pure Fab'-S-40K PEG complex comprising 40-kDa PEG linked to an —SH group of the Fab'.

Experimental Example 1: Identification and Quantitative Analysis of the Protein Conjugates <1-1> Identification of the Protein Conjugates The protein conjugates prepared in the above Examples were analyzed by non-reduced SDS-PAGE using a 4-20% gradient gel and a 12% gel and ELISA (R&D System).

Figure 3:
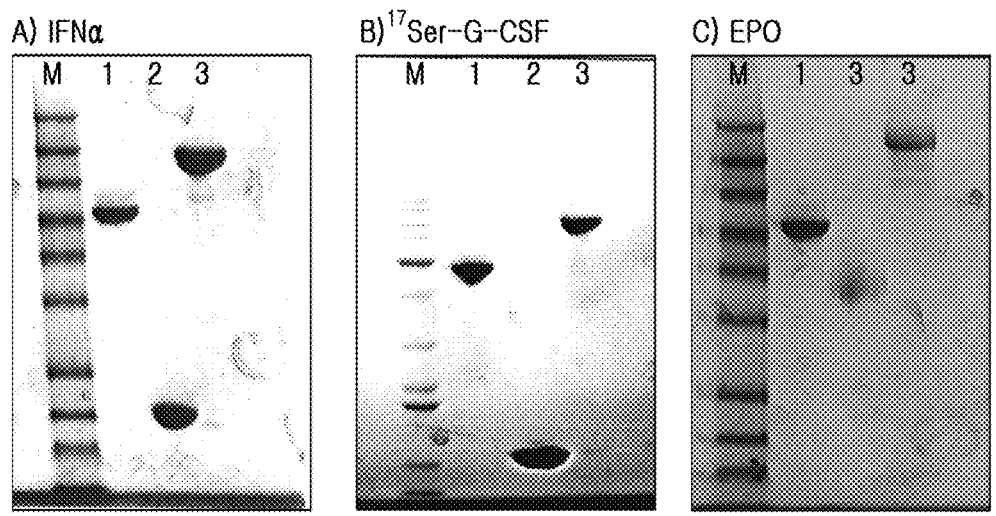
FIG. 3 shows the results of SDS-PAGE of IFNα-PEG-Fc (A), $^{17}$Ser-G-CSF-PEG-Fc (B) and EPO-PEG-Fc (C) conjugates, which are generated by a coupling reaction (M: molecular size marker, lane 1: Fc, lane 2: physiologically active protein, lane 3: physiologically active protein-PEG-Fc conjugate)

As a result of SDS-PAGE analysis, as shown in FIG. 3, a coupling reaction of a physiological polypeptide, a non-peptide polymer, PEG, and an immunoglobulin Fc fragment resulted in the successful production of an IFNα-PEG-Fc conjugate (A), a [17]Ser-G-CSF-PEG-Fc conjugate (B) and an EPO-PEG-Fc conjugate (C).

In addition, the DG Fc prepared in Example 10 was analyzed by non-reduced 12% SDS-PAGE. As shown in FIG. 6b, a DG Fc band was detected at a position, which corresponds to the molecular weight of the native Fc lacking sugar moieties.

<1-2> Quantitative Analysis of the Protein Conjugates

Figure 4:
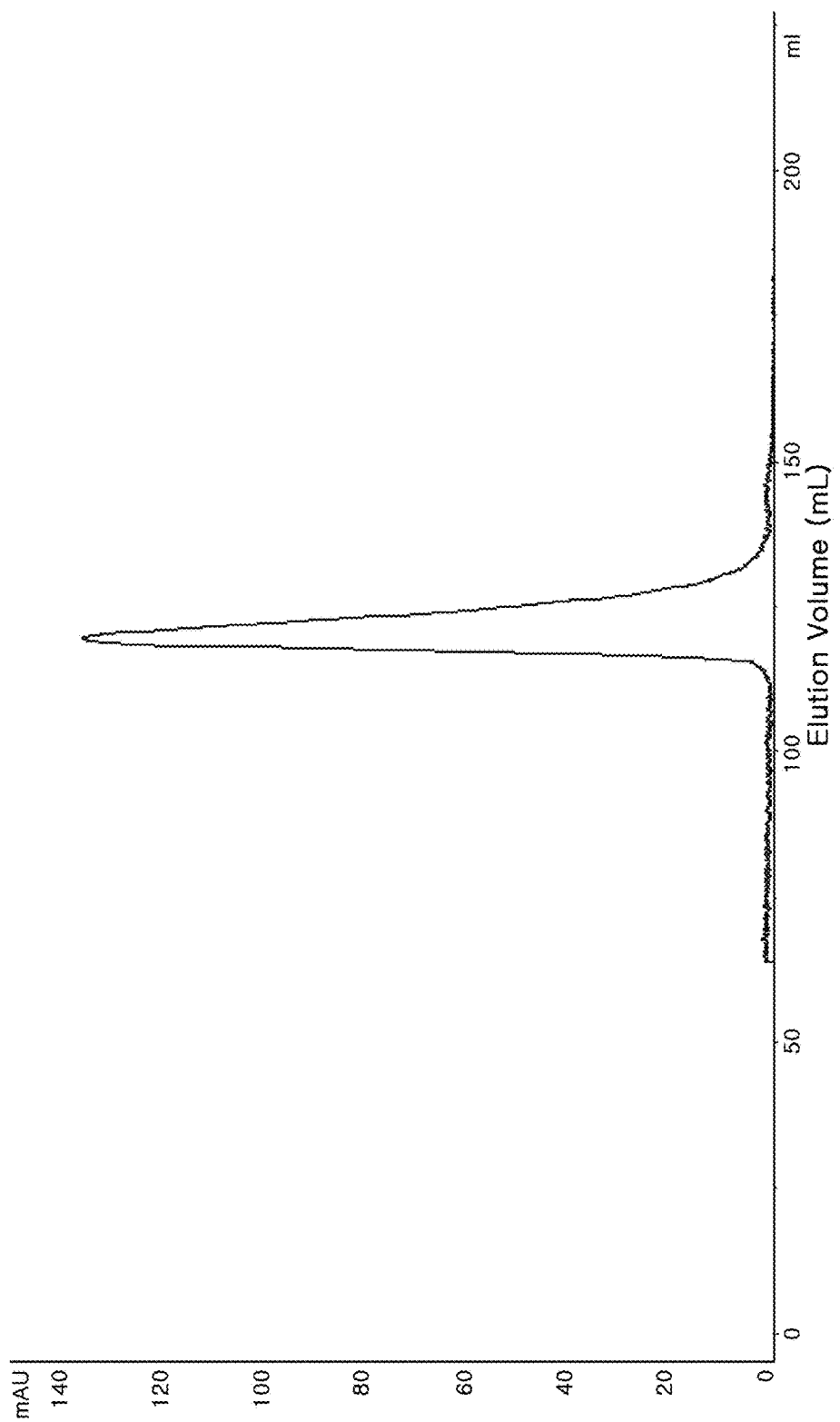
FIG. 4 shows the results of size exclusion chromatography of an IFNα-PEG-Fc conjugate that is purified after a coupling reaction.

The protein conjugates prepared in the above Examples were quantified by size exclusion chromatography using a HiLoad 26/60 Superdex 75 column (Pharmacia) and 10 mM potassium phosphate buffer (pH 6.0) as an elution buffer, wherein a peak area of each protein conjugate was compared to that of a control group. Previously quantitatively analyzed standards, IFNα, hGH, G-CSF, [17]S-G-CSF, EPO and Fc, were individually subjected to size exclusion chromatography, and a conversion factor between a concentration and a peak was determined. A predetermined amount of each protein conjugate was subjected to the same size exclusion chromatography. By subtracting a peak area corresponding to an immunoglobulin Fc fragment from the thus-obtained peak area, a quantitative value for a physiologically active protein present in each protein conjugate was determined. FIG. 4 shows the result of size exclusion chromatography of the purified IFNα-PEG-Fc conjugate, wherein a single peak was observed. This result indicates that the purified protein conjugate does not contain multimeric impurities such as a dimer, a trimer or a higher number of monomers.

When a physiologically active polypeptide conjugated to Fc was quantitatively analyzed using an antibody specific to the physiologically active polypeptide, the antibody was prevented from binding to the polypeptide, resulting in a value lower than an actual value calculated by the chromatography. In the case of the IFNα-PEG-Fc conjugate, an ELISA resulted in an ELISA value corresponding to about 30% of an actual value.

<1-3> Evaluation of Purity and Mass of the Protein Conjugates

The protein conjugates prepared in the above Examples were subjected to size exclusion chromatography, and absorbance was measured at 280 nm. As a result, the IFNα-PEG-Fc, hGH-PEG-Fc, G-CSF-PEG-Fc and [17]Ser-G-CSF-PEG-Fc conjugates displayed a single peak at the retention time of a 70 to 80-kDa substance.

On the other hand, reverse phase HPLC was carried out to determine purities of the protein conjugates prepared in Examples 1, 11 and 13, IFNα-PEG-Fc, IFNα-PEG-DG Fc and IFNα-PEG-recombinant AG Fc derivative. A reverse phase column (259 VHP54 column, Vydac) was used. The column was eluted with a 40-100% acetonitrile gradient with 0.5% TFA, and purities were analyzed by measuring absorbance at 280 nm. As a result, as shown in FIG. 8, the samples contain no unbound interferon or immunoglobulin Fc, and all of the protein conjugates, IFNα-PEG-Fc (A), IFNα-PEG-DG Fc (B) and IFNα-PEG-recombinant AG Fc derivative (C), were found to have a purity greater than 96%.

To determine accurate molecular weights of the purified protein conjugates, mass for each conjugate was analyzed using a high-throughput MALDI-TOF mass spectrophotometer (Voyager DE-STR, Applied Biosystems). Sinapinic acid was used as a matrix. 0.5 μl of each test sample was coated onto a sample slide and air-dried, again mixed with the equal volume of a matrix solution and air-dried, and introduced into an ion source. Detection was carried out in a positive fashion using a linear mode TOF analyzer. Ions were accelerated with a split extraction source operated with delayed extraction (DE) using a delayed extraction time of 750 nsec to 1500 nsec at a total acceleration voltage of about 2.5 kV.

Figure 5:
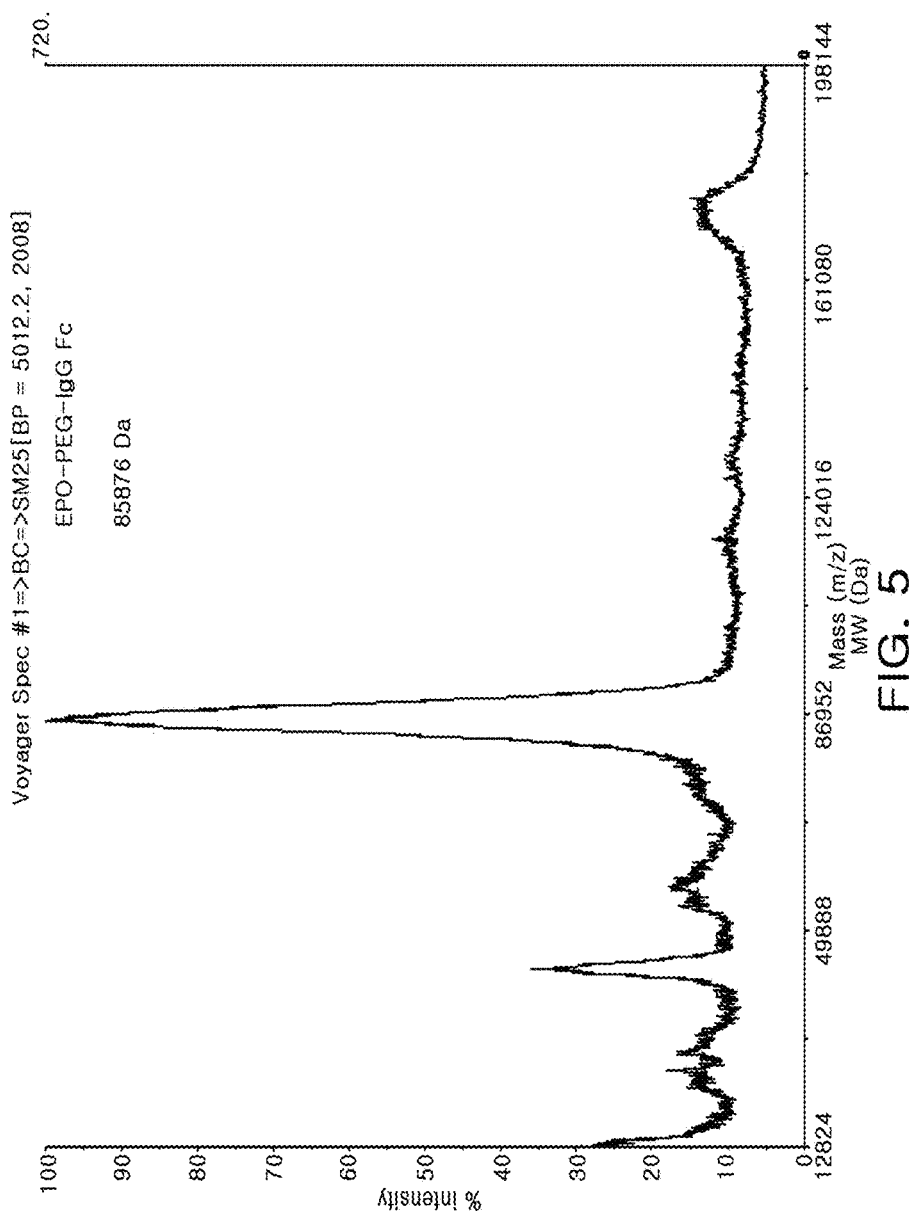
FIG. 5 shows the results of MALDI-TOF mass spectrometry of an EPO-PEG-Fc conjugate.
Figure 7:
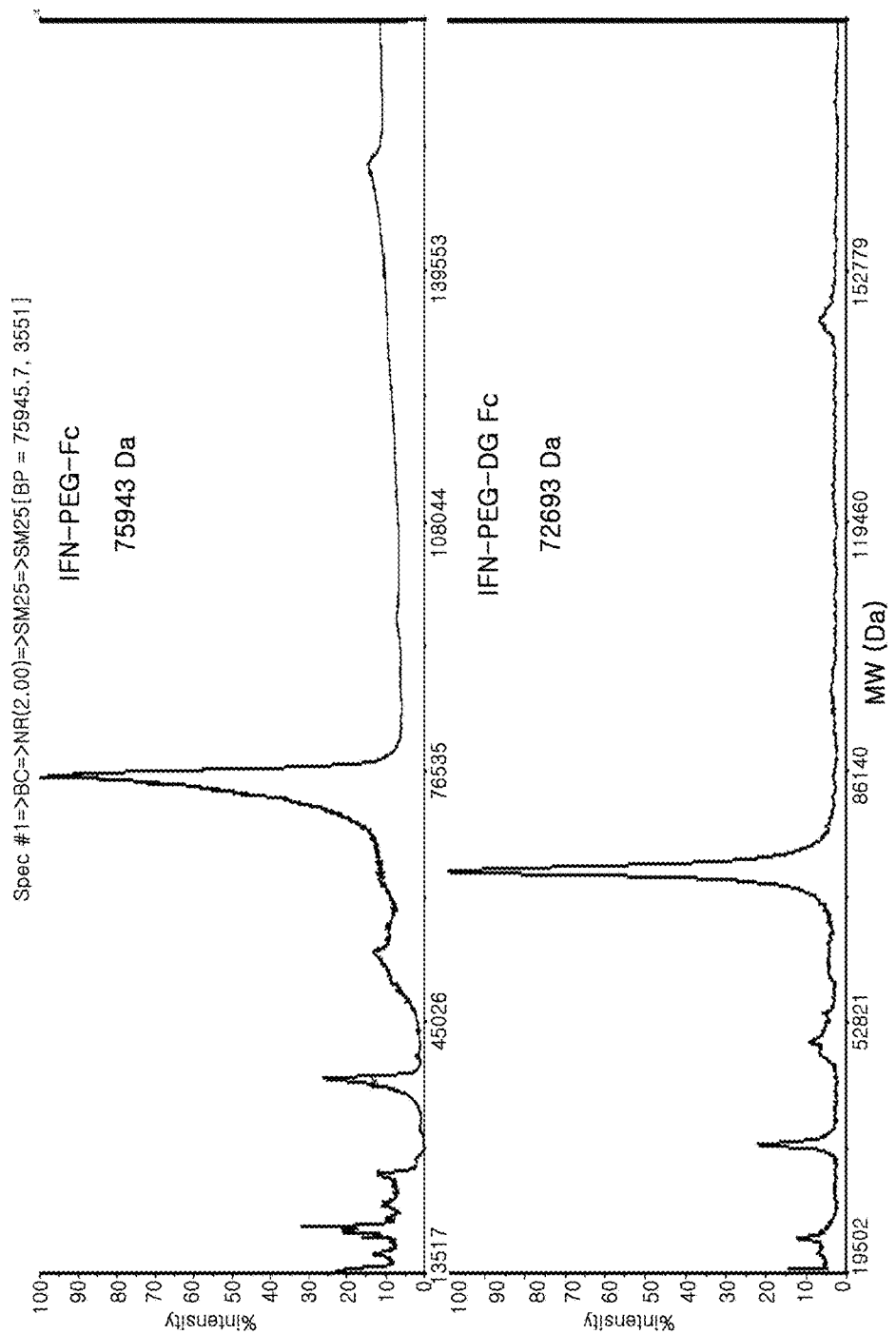
FIG. 7 shows the results of MALDI-TOF mass spectrometry of an IFNα-PEG-Fc conjugate and an IFNα-PEG-DG Fc conjugate.

The molecular weights observed by MALDI-TOF mass spectrometry for the Fc protein conjugates prepared in Examples are given in Table 1, below. FIG. 5 shows the result of MALDI-TOF mass spectrometry of the EPO-PEG-Fc conjugate, and FIG. 7 shows the results of MALDI-TOF mass spectrometry of the IFNα-PEG-Fc and IFNα-PEG-DG Fc conjugates. As a result, the EPO-PEG-Fc protein conjugate was found to have a purity of more than 95% and a molecular weight very close to a theoretical MW. Also, EPO was found to couple to the immunoglobulin Fc fragment at a ratio of 1:1.

TABLE 1

|  | Theoretical MW (kDa) | Measured MW (kDa) |
|---|---|---|
| IFNα-PEG-Fc (E.1) | 75.4 | 75.9 |
| hGH-PEG-Fc (E.3) | 78.4 | 78.6 |
| G-CSF-PEG-Fc (E.4) | 75.3 | 75.9 |
| [17]S-G-CSF derivative-PEG-Fc (E.4) | 75.0 | 75.9 |
| EPO-PEG-Fc (E.5) | 91.4 | 91.0 |

Figure 6A:
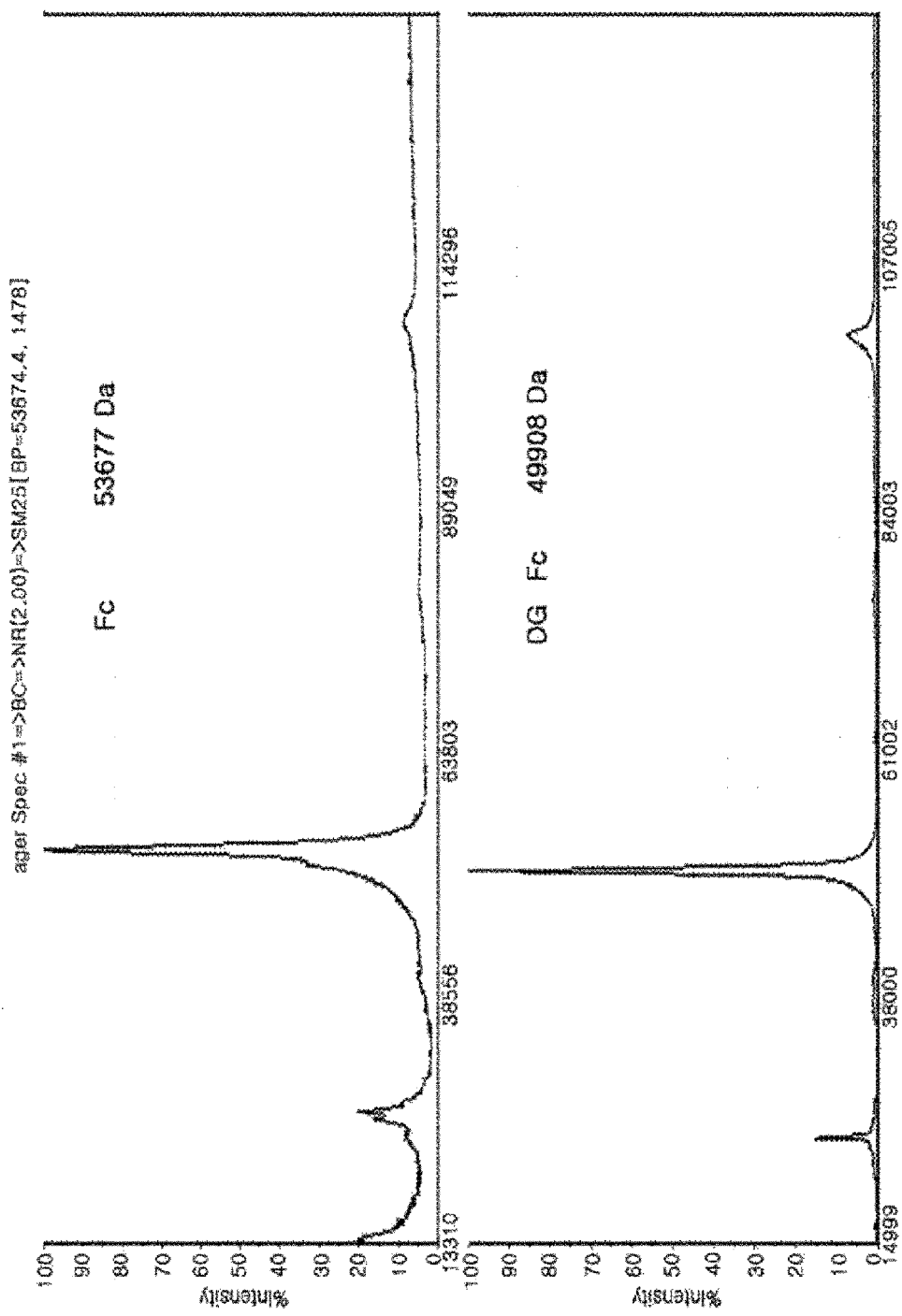
FIGS. 6a and 6b show the results of MALDI-TOF mass spectrometry and SDS-PAGE analysis, respectively, of a native immunoglobulin Fc and a deglycosylated immunoglobulin Fc (DG Fc)
Figure 6B:

In addition, when the Fc and DG Fc prepared in Example 10 were examined for their molecular weights by MALDI-TOF mass spectrometry, the DG Fc was found to be 50 kDa, which is about 3-kDa less than native Fc (FIG. 6a). Since the 3-kDa MW corresponds to the theoretical size of sugar moieties, the results demonstrate that the sugar moieties are completely removed.

Table 2, below, shows the results of MALDI-TOF mass spectrometry of the IFNα-PEG-DG Fc conjugate prepared in Example 11 and the IFNα-PEG-recombinant AG Fc derivative conjugates (I and II) prepared in Example 13. The IFNα-PEG-DG Fc conjugate was found to be 3 kDa lighter, and the IFNα-PEG-recombinant AG Fc derivative conjugate (I) to be about 3-4 kDa lighter, than the IFNα-PEG-Fc conjugate of 75.9 kDa. The IFNα-PEG-recombinant AG Fc derivative conjugate (II) coupled to an Fc monomer showed a molecular weight decreased by 24.5 kDa corresponding to the molecular weight of the Fc monomer.

TABLE 2

|  | Theoretical MW (kDa) | Measured MW (kDa) |
|---|---|---|
| IFNα-PEG-DG Fc (E.11) | 72.8 | 73.0 |
| IFNα-PEG-recombinant AG Fc derivative (I) (E.13) | 72.3 | 72.2 |
| IFNα-PEG-recombinant AG Fc derivative (II) (E.13) | 46.8 | 46.6 |

Experimental Example 2: Pharmacokinetic Analysis I

Native forms of physiologically active proteins (controls) and the protein conjugates prepared in Examples and Comparative Examples, -40K PEG complexes, -PEG-albumin conjugates, -PEG-Fc conjugates, -PEG-DG Fc conjugates and -PEG-recombinant AG Fc derivative conjugates, were evaluated for serum stability and pharmacokinetic parameters in SD rats (five rats per group). The controls, and the -40K PEG complexes, -PEG-albumin conjugates, -PEG-Fc conjugates, -PEG-DG Fc conjugates and -PEG-recombinant AG Fc derivative conjugates (test groups) were individually injected subcutaneously at a dose of 100 µg/kg. After the subcutaneous injection, blood samples were collected at 0.5, 1, 2, 4, 6, 12, 24, 30, 48, 72 and 96 hrs in the control groups, and, in the test groups, at 1, 6, 12, 24, 30, 48, 72, 96, 120, 240 and 288 hrs. The blood samples were collected in tubes with an anticoagulant, heparin, and centrifuged for 5 min using an Eppendorf high-speed micro centrifugator to remove blood cells. Serum protein levels were measured by ELISA using antibodies specific to the physiologically active proteins.

The results of pharmacokinetic analyses of the native forms of IFNα, hGH, G-CSF and EPO, and -40K PEG complexes thereof, -PEG-albumin conjugates thereof, -PEG-Fc conjugates thereof and -PEG-DG Fc conjugates thereof, are given in Tables 3 to 7, below. In the following tables, $T_{max}$ indicates the time taken to reach the maximal drug serum concentration, $T_{1/2}$ indicates the serum half-life of a drug, and MRT (mean residence time) indicates the mean time that a drug molecule resides in the body.

TABLE 3

Pharmacokinetics of interferon alpha

|  | Native IFNα | IFNα-40K PEG (C.E.1) | IFNα-PEG-albumin (C.E.2) | IFNα-PEG-Fc (E.1) | IFNα-PEG-DG Fc (E.11) | IFNα-PEG-recombinant AG Fc derivative (I) (E.13) | IFNα-PEG-recombinant AG Fc derivative (II) (E.13) |
|---|---|---|---|---|---|---|---|
| $T_{max}$ (hr) | 1.0 | 30 | 12 | 30 | 48 | 24 | 24 |
| $T_{1/2}$ (hr) | 1.7 | 35.8 | 17.1 | 90.4 | 71.0 | 61.2 | 31.2 |
| MRT (hr) | 2.1 | 71.5 | 32.5 | 150.1 | 120.6 | 111.0 | 58.8 |

TABLE 4

Pharmacokinetics of human growth factor

|  | Native hGH | hGH-40K PEG (C.E.1) | hGH-PEG-albumin (C.E.2) | hGH-PEG-Fc (E.3) |
|---|---|---|---|---|
| $T_{max}$ (hr) | 1.0 | 12 | 12 | 12 |
| $T_{1/2}$ (hr) | 1.1 | 7.7 | 5.9 | 11.8 |
| MRT (hr) | 2.1 | 18.2 | 13.0 | 18.8 |

TABLE 5

Pharmacokinetics of G-CSF

|  | Native G-CSF | G-CSF-40K PEG (C.E.1) | G-CSF-PEG-albumin (C.E.2) | G-CSF-PEG-Fc (E.4) |
|---|---|---|---|---|
| $T_{max}$ (hr) | 2.0 | 12 | 12 | 12 |
| $T_{1/2}$ (hr) | 2.8 | 4.8 | 5.2 | 6.9 |
| MRT (hr) | 5.2 | 24.5 | 25.0 | 32.6 |

TABLE 6

Pharmacokinetics of $^{17}$S-G-CSF derivative

|  | Native $^{17}$S-G-CSF derivative | $^{17}$S-G-CSF-40K PEG (C.E.1) | $^{17}$S-G-CSF-PEG-albumin (C.E.2) | $^{17}$S-G-CSF-PEG-Fc (E.4) |
|---|---|---|---|---|
| $T_{max}$ (hr) | 2.0 | 24 | 24 | 24 |
| $T_{1/2}$ (hr) | 2.9 | 4.3 | 6.4 | 7.0 |
| MRT (hr) | 5.8 | 24.4 | 25.1 | 33.2 |

TABLE 7

Pharmacokinetics of EPO

|  | Native EPO | Highly glycosylated EPO | EPO-PEG-Fc (E.5) | EPO-PEG-recombinant AG Fc derivative (E.13) |
|---|---|---|---|---|
| $T_{max}$ (hr) | 6.0 | 12 | 30 | 48 |
| $T_{1/2}$ (hr) | 9.4 | 18.4 | 61.5 | 87.9 |
| MRT (hr) | 21.7 | 26.8 | 117.6 | 141.6 |

Figure 9:
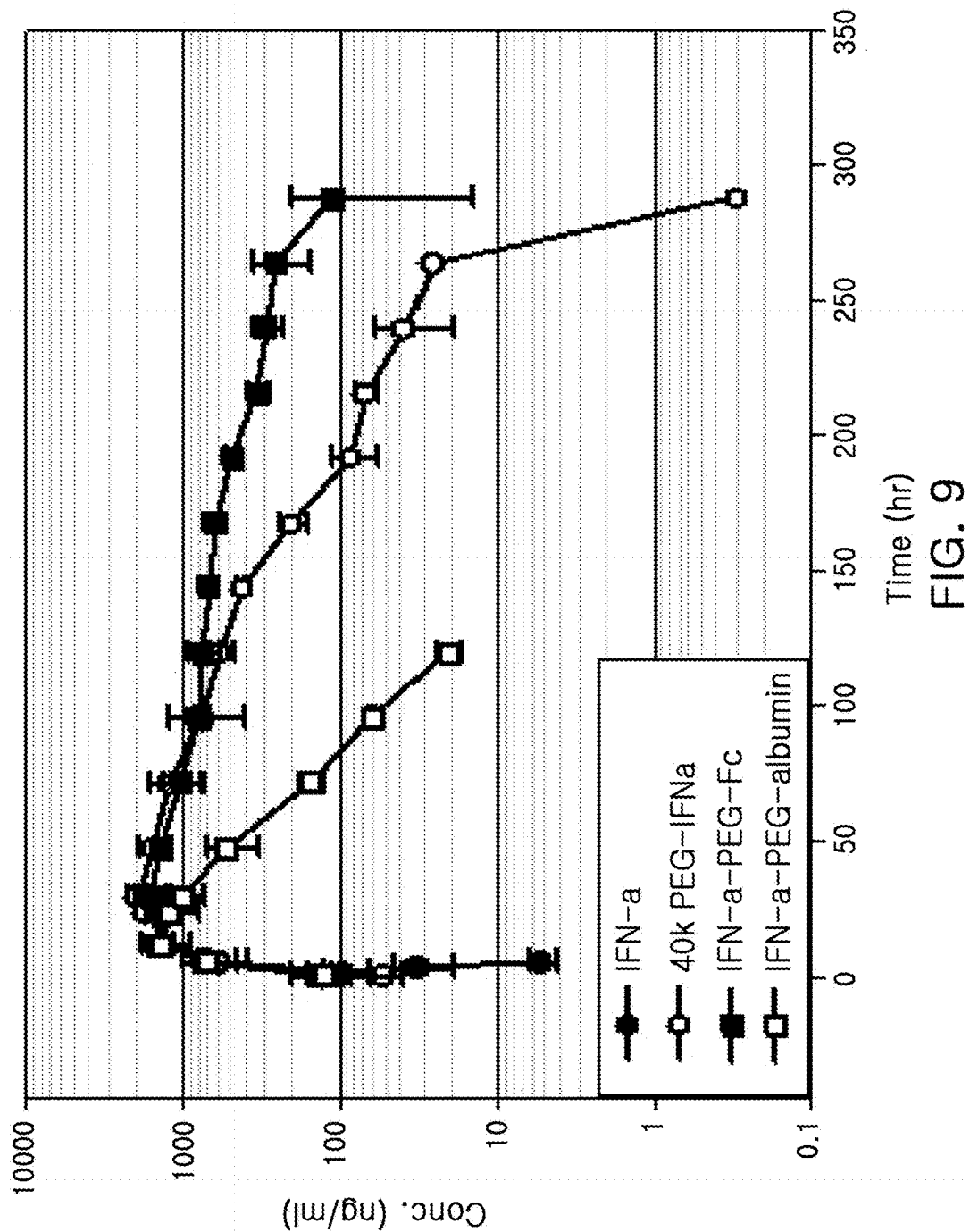
FIG. 9 is a graph showing the results of pharmacokinetic analysis of a native IFNα, an IFNα-40K PEG complex, an IFNα-PEG-albumin conjugate and an IFNα-PEG-Fc conjugate.

As shown from the data of Table 3 and the pharmacokinetic graph of FIG. 9, the IFNα-PEG-Fc protein conjugate had a serum half-life of 90.4 hrs, which was about 50 times higher than that of native IFNα and about 2.5 times higher than that of IFNα-40K PEG having a half-life of 35.8 hrs, prepared in Comparative Example 1. Also, the IFNα-PEG-Fc protein conjugate of the present invention was found to be superior in serum half-life to IFNα-PEG-albumin, which has a half-life of 17.1 hrs.

On the other hand, as shown in Table 3 and FIG. 11, the IFNα-PEG-DG Fc conjugate had a serum half-life of 71.0 hrs, which was almost the same as the IFNα-PEG-Fc conjugate, indicating that the deglycosylation of Fc does not greatly affect the in vivo stability of the IFNα-PEG-DG Fc conjugate. Also, the conjugate prepared using the recombinant AG Fc derivative produced by a recombinant method was found to have an effect identical to that of the native form-derived DG Fc. However, the serum half-life of a complex coupled to an Fc monomer was about half that of a complex coupled to a normal Fc dimer.

As shown in Table 4, human growth hormone also showed an extended serum half-life when conjugated to the IgG Fc fragment according to the present invention. That is, compared to the native form (1.1 hrs), the hGH-40K PEG complex and hGH-PEG-albumin conjugate had slightly increased half-lives of 7.7 hrs and 5.9 hrs, respectively, whereas the hGH-PEG-Fc protein conjugate of the present invention displayed a greatly extended serum half-life of 11.8 hrs.

As apparent from the pharmacokinetic data of G-CSF and its derivative in Table 5 and 6, the G-CSF-PEG-Fc and $^{17}$S-G-CSF-PEG-Fc conjugates displayed a much longer serum half-life than the -40K PEG complex and -PEG-albumin conjugate. The immunoglobulin Fc fragment was found in the serum to prolong the duration of action of physiologically active proteins in native forms, as well as in their derivatives having alterations of certain amino acid residues in similar levels to the native forms. From these results, it is easily predictable that the method of the present invention will have a similar effect on other proteins and their derivatives.

Figure 10:
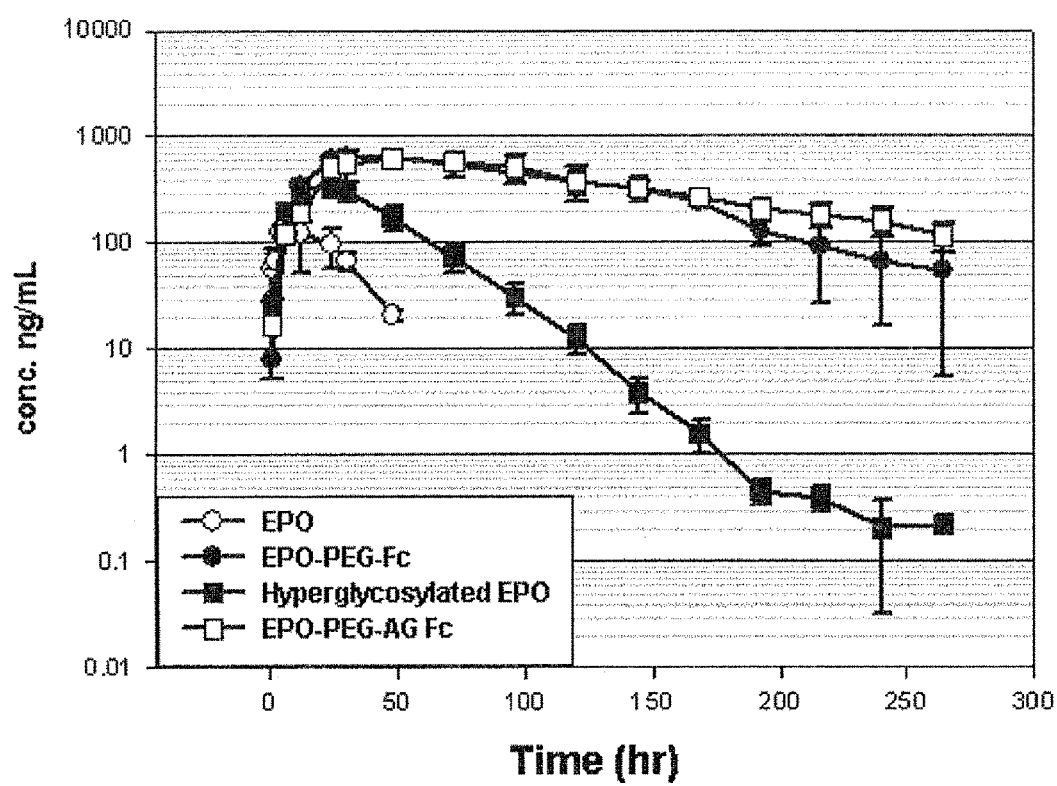
FIG. 10 is a graph showing the results of pharmacokinetic analysis of a native EPO, a highly glycosylated EPO, an EPO-PEG-Fc conjugate and an EPO-PEG-AG Fc conjugate.

As shown in Table 7 and FIG. 10, the conjugation of the native glycosylated EPO to the Fc fragment also resulted in an increase in serum half-life. That is, EPO had a serum half-life of 9.4 hrs in the native form, and a prolonged serum half-life of 18.4 hrs when highly glycosylated to improve serum stability. The EPO-PEG-Fc conjugate, comprising EPO coupled to the immunoglobulin Fc fragment according to the present invention, displayed a markedly prolonged serum half-life of 61.5 hrs. Also, when conjugated to the *E. coli*-derived recombinant aglycosylated (AG) Fc derivative, the half-life of EPO increased to 87.9 hrs, indicating that the aglycosylation of the Fc fragment allows the preparation of a protein conjugate not affecting serum stability of the protein without antibody functions.

As apparent from the above results, the protein conjugates covalent-bonded to the immunoglobulin Fc fragment through a non-peptide polymer according to the present invention displayed serum half-lives increased several to several tens to that of the native form. Also, when the immunoglobulin Fc was aglycosylated by production in *E. coli* or deglycosylated by enzyme treatment, its effect of increasing the serum half-life of its protein conjugate was maintained at a similar level.

In particular, compared to proteins modified with 40-kDa PEG having the longest duration of action among PEG molecules for increasing the duration of action of proteins in the serum, the immunoglobulin Fc protein conjugates had much superior serum stability. In addition, compared to protein conjugates coupled to albumin instead of the immunoglobulin Fc, the protein conjugates of the present invention displayed excellent serum stability, indicating that the protein conjugates of the present invention are effective in developing long-acting forms of protein drugs. These results, that the present protein conjugates have excellent effects on serum stability and MRT in a broad range of proteins including colony stimulating factor derivatives by point mutation compared to conventional PEG- or albumin-conjugated proteins, indicate that the stability and duration-extending effects of the present protein conjugates are applicable to other physiologically active polypeptides.

On the other hand, when the IFNα-10K PEG-Fc protein conjugate (Example 7) prepared using a non-peptide polymer, 10-kDa PEG, was evaluated for its serum half-life according to the same method as described above, it showed a serum half-life of 48.8 hrs, which was somewhat shorter than the serum half-life (79.7 hrs) of a protein conjugate prepared using 3.4-kDa PEG.

In addition, the serum half-lives of the protein conjugates decrease with increasing molecular weight of the non-peptide polymer PEG. These results indicate that the major factor increasing the serum stability and duration of the protein conjugates is the conjugated immunoglobulin Fc fragment rather than the non-peptide polymer.

Even when the reactive group of PEG was exchanged with a reactive group other than the aldehyde group, protein conjugates with the PEG showed similar patterns in apparent molecular weight and serum half-life to those coupled to PEG having an aldehyde reactive group.

Experimental Example 3: Pharmacokinetic Analysis II

To determine the serum half-lives of the Fab'-S-PEG-N-Fc and Fab'-N-PEG-N-Fc conjugates prepared in Example 8 and 9 and the Fab'-S-40K PEG complex prepared in Comparative Example 3, drug pharmacokinetic analysis was carried out according to the same method as in Experimental Example 2 using Fab' as a control, the conjugates and the complex. The results are given in FIG. 12.

As shown in FIG. 12, the Fab'-S-PEG-N-Fc and Fab'-N-PEG-N-Fc conjugates displayed a serum half-life prolonged two or three times compared to the Fab' or Fab'-S-40K PEG complex.

Experimental Example 4: Evaluation of Intracellular Activity of the Protein Conjugates <4-1> Comparison of the IFN Protein Conjugates for Intracellular Activity To compare the intracellular activity of the IFNα protein conjugates, the IFNα-PEG-Fc (Example 1), IFNα-PEG-DG Fc (Example 11), IFNα-PEG-recombinant AG Fc derivative (Example 13), IFNα-40K PEG (Comparative Example 1) and IFNα-PEG-albumin (Comparative Example 2) were evaluated for antiviral activity by a cell culture bioassay using Madin Darby Bovine Kidney (MDBK) cells (ATCC CCL-22) infected with vesicular stomatitis virus. Nonpegylated interferon alpha-2b, available from the National Institute for Biological Standards and Controls (NIBSC), was used as a standard material.

MDBK cells were cultured in MEM (minimum essential medium, JBI) supplemented with 10% FBS and 1% penicillin/streptomycin at 37° C. under 5% $CO_2$ condition. Samples to be analyzed and the standard material were diluted with the culture medium to predetermined concentrations, and 100-μl aliquots were placed onto each well of a 96-well plate. The cultured cells were detached, added to the plate containing the samples in a volume of 100 μl, and cultured for about 1 hr at 37° C. under 5% $CO_2$ condition. Then, 50 μl of vesicular stomatitis virus (VSV) of $5$-$7 \times 10^3$ PFU was added to each well of the plate, and the cells were further cultured for about 16 to 20 hrs at 37° C. under 5% $CO_2$ conditions. A well that did not contain the sample or standard material but contained only the virus was used as a negative control, and a well that contained only cells was used as a positive control.

After the culture medium was removed, 100 μl of a neutral red solution was added to the plate to stain viable cells, followed by incubation for 2 hrs at 37° C. under 5% $CO_2$ condition. After the supernatants were removed, 100 μl of a 1:1 mixture of 100% ethanol and 1% acetic acid was added to each well of the plate. After thorough mixing to dissolve all neutral red crystals eluted from stained cells, absorbance was measured at 540 nm. The negative control was used as a blank, and $ED_{50}$ values (doses causing 50% cell growth inhibition) were calculated, where the cell growth of the positive control was set at 100%.

TABLE 8

| | Conc. (ng/ml) | Specific activity (IU/mg) | Relative activity (%) for native IFNα |
|---|---|---|---|
| Native IFNα | 100 | 4.24E+08 | 100 |
| IFNα-40K PEG | 100 | 2.04E+07 | 4.8 |
| IFNα-PEG-albumin | 100 | 2.21E+07 | 5.2 |
| IFNα-PEG-Fc | 100 | 1.19E+08 | 28.1 |
| IFNα-PEG-DG Fc | 100 | 1.09E+08 | 25.7 |
| IFNα-PEG-recombinant AG Fc derivative | 100 | 9.58E+07 | 22.6 |

As shown in Table 8, the IFNα-40K PEG decreased in activity to 4.8% of the native IFNα. Especially, as the size of the PEG moieties increased, a protein conjugate has improved serum stability but gradually decreased activity. Interferon alpha was reported to have in vitro activities of 25% when modified with 12-kDa PEG and about 7% when modified with 40-kDa PEG (P. Bailon et al., *Bioconjugate Chem.* 12: 195-202, 2001). That is, since a protein conjugate has a longer half-life but sharply decreases in biological activity as the molecular weight of PEG moieties increase, there is a need for the development of a protein conjugate having a longer serum half-life and a stronger activity. In addition, the IFNα-PEG-albumin conjugate displayed a weak activity of about 5.2% compared to the native IFNα. In contrast, the IFNα-PEG-Fc and IFNα-PEG-DG Fc conjugates of the present invention exhibited a markedly improved relative activity of 28.1% and 25.7% compared to the native IFNα. Also, the conjugation of IFNα to the recombinant AG Fc derivative resulted in a similar increase in activity. From these results, it is expected that interferon alpha conjugated to the immunoglobulin Fc fragment has a markedly increased serum half-life and greatly improved pharmaceutical efficacy in vivo.

<4-2> Comparison of the Human Growth Hormone Protein Conjugates for Intracellular Activity To compare the intracellular activity of the human growth hormone protein conjugates, the hGH-PEG-Fc, hGH-40K PEG and hGH-PEG-albumin were compared for intracellular activity.

Intracellular activities of the hGH conjugates were measured by an in vitro assay using a rat node lymphoma cell line, Nb2 (European Collection of Cell Cultures (ECACC) #97041101), which develops human growth hormone-dependent mitogenesis.

Nb2 cells were cultured in Fisher's medium supplemented with 10% FBS (fetal bovine serum), 0.075% $NaCO_3$, 0.05 mM 2-mercaptoethanol and 2 mM glutamin, and were further cultured in a similar medium not containing 10% FBS for 24 hrs. Then, the cultured cells were counted, and about $2 \times 10^4$ cells were aliquotted onto each well of a 96-well plate. The hGH-PEG-Fc, the hGH-40K PEG, the hGH-PEG-albumin, a standard available from the National Institute for Biological Standards and Controls (NIBSC) as a control, and native human growth hormone (HM-hGH) were diluted and added to each well at various concentrations, followed by incubation for 48 hrs at 37° C. under 5% $CO_2$ condition. Thereafter, to measure cell proliferation activity by determining the cell number in each well, 25 μl of the Cell Titer 96 Aqueous One Solution Reagent (Promega) was added to each well, and the cells were further cultured for 4 hrs. Absorbance was measured at 490 nm, and a titer for each sample was calculated. The results are given in Table 9, below.

TABLE 9

|  | Conc. (ng/ml) | Specific activity* (U/mg) | Relative activity (%) for native HM-hGH |
|---|---|---|---|
| Native hGH | 100 | 2.71E+06 | 100 |
| hGH (standard available from NIBSC) | 100 | 2.58E+06 | 95.2 |
| hGH-40K PEG | 100 | 0.206E+06 | 7.6 |
| hGH-PEG-albumin | 100 | 0.141E+06 | 5.2 |
| hGH-PEG-Fc | 100 | 0.76E+06 | 28.1 |

Specific activity* = $1/ED_{50} \times 10^6$ ($ED_{50}$: protein amount required for 50% of maximum cell growth)

As shown in Table 9, also in the case of human growth hormone, the conjugation to 40-kDa PEG (hGH-40K PEG) resulted in a decrease in activity to about 7.6% of the native form, and the hGH-PEG-albumin conjugate displayed a low in vitro activity that was about 5.2% of the native hGH. However, the hGH-PEG-Fc conjugate of the present invention markedly increased in relative activity to greater than 28% compared to the native hGH. From these results, it is expected that human growth hormone linked to the immunoglobulin Fc fragment has a markedly increased serum half-life and a greatly improved in vivo pharmaceutical efficacy. In addition, it is believed that the increased activity of the immunoglobulin Fc protein conjugates of the present invention is due to the increased serum stability and preserved binding affinity to receptors due to the immunoglobulin Fc or due to the space formed by the non-peptide polymer. These effects are predicted to be applicable to immunoglobulin Fc protein conjugates coupled to other physiologically active proteins.

<4-3> Comparison of the G-CSF Protein Conjugates for Intracellular Activity

To compare the intracellular activity of the protein conjugates with a G-CSF derivative, the native G-CSF (Filgrastim, Jeil Pharm. Co., Ltd.), $^{17}$Ser-G-CSF derivative, 20K PEG-G-CSF (Neulasta), 40K PEG-$^{17}$S-G-CSF, $^{17}$Ser-G-CSF-PEG-albumin and $^{17}$S-G-CSF-PEG-Fc were compared for intracellular activity.

First, a human myeloid cell line, HL-60 (ATCC CCL-240, promyelocytic leukemia patient/36 yr old Caucasian female), was cultured in RPMI 1640 medium supplemented with 10% FBS. The cultured cells were suspended at a density of about $2.2 \times 10^5$ cells/ml, and DMSO (dimethylsulfoxide, culture grade, Sigma) was added thereto at a final concentration of 1.25% (v/v). Then, 90 μl of the cell suspension was seeded onto each well of a 96-well plate (Corning/low evaporation 96 well plate), thus providing a density of about $2 \times 10^4$ cells per well, and cultured in an incubator at 37° C. with 5% $CO_2$ for about 72 hrs.

Each sample, whose protein concentration was determined using a G-CSF ELISA kit (R&D systems), was diluted with RPMI 1640 to an identical concentration of 10 μg/ml, and further diluted two-fold with RPMI 1640 nineteen times. The serial two-fold dilutions were individually added to each well containing HL-60 cells at a volume of 10 μl, so that the concentration of each sample started at 1 μg/ml. Then, the cells were cultured in an incubator at 37° C. for 72 hrs.

The proliferation of HL-60 cells was assayed using Cell Titer 96™ (Cat. NO. G4100, Promega), and the increased cell number was determined by measuring absorbance at 670 nm.

TABLE 10

|  | $ED_{50}$ (IU/mg) | Relative activity (%) for native G-CSF |
|---|---|---|
| Native G-CSF | 0.30 | 100 |
| $^{17}$Ser-G-CSF | 0.26 | 115 |
| G-CSF-20K PEG (Neulasta) | 1.20 | 25 |
| $^{17}$Ser-G-CSF-40K PEG | 10.0 | <10.0 |
| $^{17}$Ser-G-CSF-PEG-albumin | 1.30 | 23.0 |
| $^{17}$Ser-G-CSF-PEG-Fc | 0.58 | 51.7 |

As shown in Table 10, the immunoglobulin Fc protein conjugates coupled to a G-CSF derivative having an amino acid substitution, $^{17}$Ser-G-CSF, also displayed similar effects to native G-CSF-coupled protein conjugates. The $^{17}$Ser-G-CSF-PEG was previously reported to have a relatively increased serum half-life but a decreased activity compared to nonpegylated [17]Ser-G-CSF (Korean Pat. Laid-open Publication No. 2004-83268). Especially, as the size of the PEG moieties increased, a protein conjugate had increased serum stability but gradually decreased activity. The [17]Ser-G-CSF-40K PEG showed a very low activity of less than about 10% compared to the native form. That is, since a protein conjugate has an extended serum half-life but a sharply decreased activity as the molecular weight of PEG moieties increases, there is the need for the development of a protein conjugate having a long serum half-life and strong activity. The [17]Ser-G-CSF-PEG-albumin also showed a low activity of about 23% compared to the native G-CSF. In contrast, the [17]Ser-G-CSF-PEG-Fc was greatly improved in relative activity to more than 51% compared to the native G-CSF. From these results, it is expected that [17]Ser-G-CSF linked to the immunoglobulin Fc fragment has a markedly increased serum half-life and a greatly improved pharmaceutical in vivo efficacy.

<4-4> Cytotoxicity Neutralization Assay for the Fab' Conjugates

An in vitro activity assay was carried out using the Fab'-S-PEG-N-Fc and Fab'-N-PEG-N-Fc conjugates prepared in Example 8 and 9 and the Fab'-S-40K PEG complex prepared in Comparative Example 3. Through a cytotoxicity assay based on measuring TNFα-mediated cytotoxicity, the Fab' conjugates were evaluated to determine whether they neutralize TNFα-induced apoptosis in a mouse fibroblast cell line, L929 (ATCC CRL-2148).

The Fab'-S-PEG-N-Fc and Fab'-N-PEG-N-Fc conjugate and the Fab'-S-40K PEG complex were serially two-fold diluted, and 100-μl aliquots were placed onto wells of a 96-well plate. rhTNF-α (R&D systems) and actinomycin D (Sigma) used as an RNA synthesis inhibitor were added to each well at final concentrations of 10 ng/ml and 1 μg/ml, respectively, incubated for 30 min in an incubator at 37° C. with 5% $CO_2$, and transferred to a microplate for assay. L929 cells were added to each well at a density of $5\times10^4$ cells/50 μl medium and cultured for 24 hrs in an incubator at 37° C. with 5% $CO_2$. After the culture medium was removed, 50 μl of MTT (Sigma) dissolved in PBS at a concentration of 5 mg/ml was added to each well, and the cells were further cultured for about 4 hrs in an incubator at 37° C. with 5% $CO_2$. 150 μl of DMSO was added to each well, and the degree of cytotoxicity neutralization was determined by measuring the absorbance at 540 nm. As a control, the Fab' purified in the step 1 of Example 8 was used.

Figure 13:
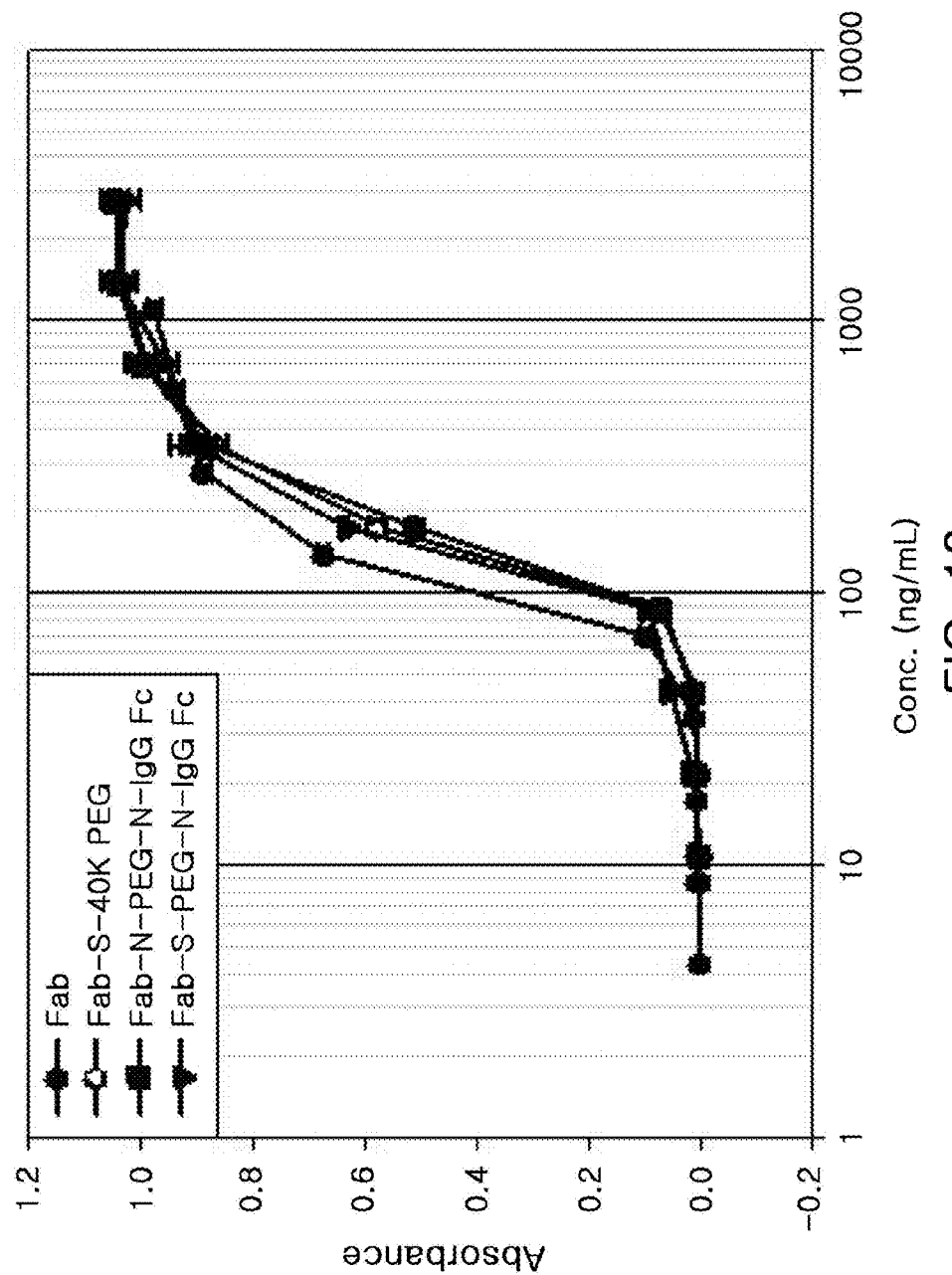
FIG. 13 is a graph showing the in vivo activities of Fab', a Fab'-S-40K PEG complex, a Fab'-N-PEG-N-Fc conjugate and a Fab'-S-PEG-N-Fc conjugate.

As shown in FIG. 13, all of the protein conjugates used in this test had a similar titer to the Fab'. These results indicate that, when a protein conjugate is prepared by linking an immunoglobulin Fc to a free cysteine residue near the N-terminus or C-terminus of a Fab' through PEG, the Fab' exhibits a markedly increased serum half-life and a high in vivo activity.

<4-5> Complement-Dependent Cytotoxicity (CDC) Assay

To determine whether the derivatives prepared in Examples and proteins corresponding to the constant regions of immunoglobulins, expressed in the *E. coli* transformants and purified, bind to human C1q, an enzyme linked immunosorbent assay (ELISA) was carried out as follows. As test groups, immunoglobulin constant regions produced by the HM10932 and HM10927 transformants, deposited at the Korean Culture Center of Microorganisms (KCCM) on Sep. 15, 2004, and assigned accession numbers KCCM-10597, KCCM-10588, and the derivatives prepared in the above Examples were used. As standards, a glycosylated immunoglobulin (IVIG-globulin S, Green Cross PBM) and several commercially available antibodies used as therapeutic antibodies were used. The test and standard samples were prepared in 10 mM carbonate buffer (pH 9.6) at a concentration of 1 μg/ml. The samples were aliquotted into a 96-well plate (Nunc) in an amount of 200 ng per well, and the plate was coated overnight at 4° C. Then, each well was washed with PBS-T (137 mM NaCl, 2 mM KCl, mM $Na_2HPO_4$, 2 mM $KH_2PO_4$, 0.05% Tween 20) three times, blocked with 250 μl of a blocking buffer (1% bovine serum albumin in PBS-T) at room temperature for 1 hr, and washed again with the same PBS-T three times. The standard and test samples were diluted in PBS-T to a predetermined concentration and added to antibody-coated wells, and the plate was incubated at room temperature for 1 hr and washed with PBS-T three times. Thereafter, 2 μg/ml C1q (R&D Systems) was added to the plate and reacted at room temperature for 2 hrs, and the plate was washed with PBS-T six times. 200 μl of a 1:1000 dilution of a human anti-human C1q antibody-peroxidase conjugate (Biogenesis, USA) in the blocking buffer was added to each well and reacted at room temperature for 1 hr. After each well was washed with PBS-T three times, equal volumes of color reagents A and B (Color A: stabilized peroxide and Color B: stabilized chromogen; DY 999, R&D Systems) were mixed, and 200 μl of the mixture was added to each well, followed by incubation for 30 min. Then, 50 μl of a reaction termination solution, 2 M sulphuric acid, was added to each well. The plate was read using a microplate reader (Molecular Device). Absorbance of standard and test samples was measured at 450 nm, and the results are given in FIGS. 14 and 15, respectively.

Figure 14:
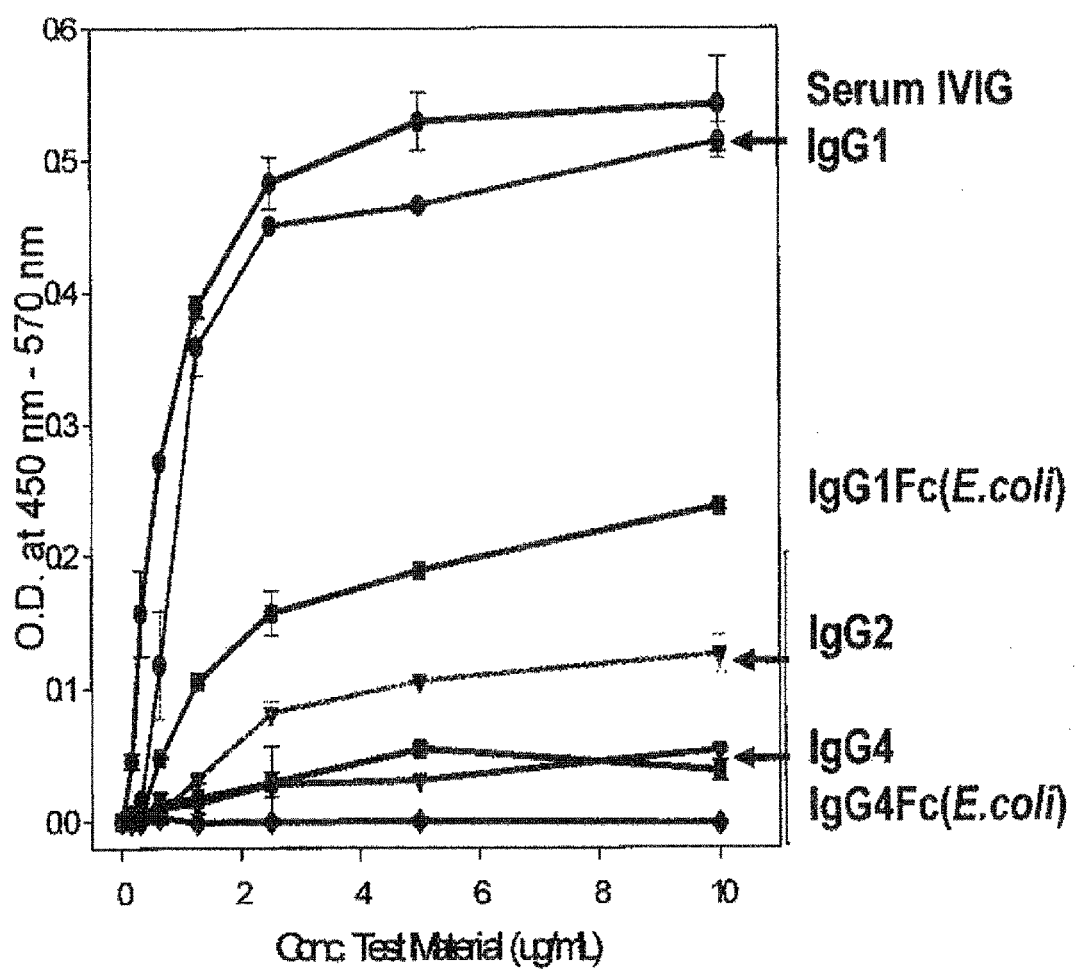
FIG. 14 is a graph showing the results of comparison of human IgG subclasses for binding affinity to the C1q complement.

When immunoglobulin subclasses were compared with each other for complement activity in their immunoglobulin Fc fragment, the highest binding affinity to C1q was found in human immunoglobulin IgG1 (Fitzgerald), the next in IgG2 (Fitzgerald) and then IgG4 (Fitzgerald), indicating that there is a difference between subclasses in complement activity. The IVIG used in this test, which is a pool of IgG subclasses, exhibited a C1q binding affinity almost the same as the purified IgG1 because IgG1 amounts to most of the IVIG. Compared to these standards, with respect to changes in binding affinity to C1q by aglycosylation, IgG1 Fc having the strongest complement activity markedly decreased when aglycosylated. IgG4 Fc, known not to induce complement activation, rarely had binding affinity to C1q, indicating that the IgG4 Fc is used as an excellent recombinant carrier with no complement activity (FIG. 14).

Figure 15:
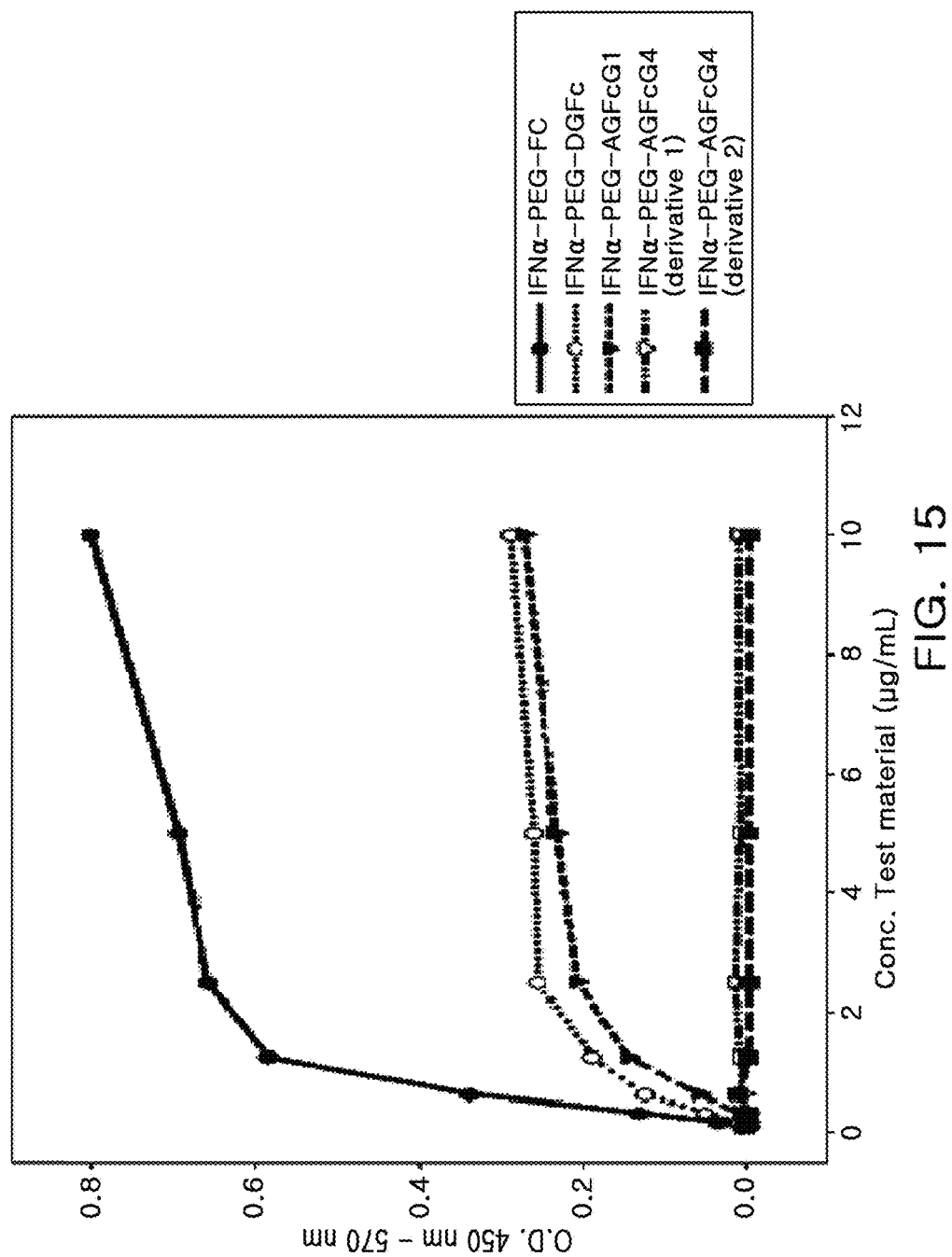
FIG. 15 is a graph showing the results of comparison of a glycosylated Fc, an enzymatically deglycosylated DG Fc and an interferon-PEG-carrier conjugate where the carrier is AG Fc produced by *E. coli* for binding affinity to the C1q complement.

To determine whether the carrier maintains its property of having no binding affinity to C1q even after being conjugated to a physiologically active peptide, IFN alpha-Fc conjugates were prepared using glycosylated Fc, enzymatically deglycosylated Fc and aglycosylated recombinant Fc as carriers for IFN alpha and were evaluated for their binding affinity to C1q. A glycosylated Fc-coupled IFN alpha conjugate (IFNα-PEG-Fc: Glycosylated IgG1Fc) maintained a high binding affinity to C1q. In contrast, when interferon alpha was coupled to an Fc deglycosylated using PNGase F and other enzymes, the resulting conjugate (IFNα-PEG-DGFc: Deglycosylated IgG1Fc) displayed a markedly decreased binding affinity to C1q, which was similar to that of the *E. coli*-derived aglycosylated Fc conjugate. In addition, when the IgG1 moiety of the aglycosylated IgG1 Fc-coupled interferon alpha conjugate (IFNα-PEG-AGFcG1: Aglycosylated IgG1Fc) was exchanged with the IgG4 moiety, the resulting interferon conjugate (IFNα-PEG-FcG4 derivative 1: Aglycosylated IgG4Fc) was found to completely lose its binding affinity to C1q. When the IgG1 Fc moiety was exchanged with the IgG4 Fc monomer, the resulting conjugate (IFNα-PEG-FcG4 derivative 2: Aglycosylated IgG4Fc). These results indicate that such forms of the IgG4 Fc fragment are useful as excellent carriers not having the effector functions of antibody fragments (FIG. 15).

INDUSTRIAL APPLICABILITY

As described hereinbefore, the protein conjugate of the present invention greatly increases plasma half-lives of polypeptide drugs to levels higher than any conventional modified proteins. On the other hand, the protein conjugates overcome the most significant disadvantage of conventional long-acting formulations, decreasing drug titers, thus having blood circulation time and in vivo activity superior to albumin, previously known to be most effective. In addition, the protein conjugates have no risk of inducing immune responses. Due to these advantages, the protein conjugates are useful for developing long-acting formulations of protein drugs. The long-acting formulations of protein drugs according to the present invention are capable of reducing the patient's pain from frequent injections, and of maintaining serum concentrations of active polypeptides for a prolonged period of time, thus stably providing pharmaceutical efficacy.

Further, the present method of preparing a protein conjugate overcomes disadvantages of fusion protein production by genetic manipulation, including difficult establishment of expression systems, glycosylation different from a native form, immune response induction and limited orientation of protein fusion, low yields due to non-specific reactions, and problems of chemical coupling such as toxicity of chemical compounds used as binders, thereby easily economically providing protein drugs with extended serum half-life and high activity.

The invention claimed is:

1. A protein conjugate comprising a physiologically active polypeptide, a non-peptide polymer and an immunoglobulin Fc fragment wherein the non-peptide polymer is covalently linked via a different reactive group at both ends thereof to the physiologically active polypeptide and the immunoglobulin Fc fragment;
wherein the non-peptide polymer ranges from 1 to 20 kDa in molecular weight;
wherein the immunoglobulin Fc fragment consists essentially of a heavy-chain constant region 2, a heavy-chain constant region 3 and a hinge region of an immunoglobulin; and
wherein the immunoglobulin Fc fragment does not contain variable regions of heavy and light chains of the immunoglobulin.

2. The protein conjugate according to claim 1, wherein the non-peptide polymer is covalently linked via a reactive group at both ends thereof to the physiologically active polypeptide and the immunoglobulin Fc fragment.

3. The protein conjugate according to claim 1, wherein one or more complexes of the physiologically active polypeptide and the non-peptide polymer are covalently linked to a single molecule of the immunoglobulin Fc fragment.

4. The protein conjugate according to claim 1, wherein the immunoglobulin Fc fragment is non-glycosylated.

5. The protein conjugate according to claim 1, wherein the immunoglobulin Fc fragment is selected from the group consisting of Fc fragments from IgG, IgA, IgD, IgE, IgM, and combinations and hybrids thereof.

6. The protein conjugate according to claim 5, wherein the immunoglobulin Fc fragment is selected from the group consisting of Fc fragments from IgG1, IgG2, IgG3, IgG4, and combinations and hybrids thereof.

7. The protein conjugate according to claim 6, wherein the immunoglobulin Fc fragment is an IgG4 Fc fragment.

8. The protein conjugate according to claim 7, wherein the immunoglobulin Fc fragment is a human aglycosylated IgG4 Fc fragment.

9. The protein conjugate according to claim 1, wherein the reactive group of the non-peptide polymer is selected from the group consisting of an aldehyde group, a propione aldehyde group, a butyl aldehyde group, a maleimide group and a succinimide derivative.

10. The protein conjugate according to claim 9, wherein the succinimide derivative is succinimidyl propionate, succinimidyl carboxymethyl, hydroxy succinimidyl or succinimidyl carbonate.

11. The protein conjugate according to claim 1, wherein the non-peptide polymer is linked at each end thereof to a free reactive group at an amino terminal end, a lysine residue, a histidine residue or a cysteine residue of the immunoglobulin Fc fragment and the physiologically active polypeptide.

12. The protein conjugate according to claim 1, wherein the non-peptide polymer is selected from the group consisting of polyethylene glycol single polymers, polypropylene glycol single polymers, ethylene glycol-propylene glycol copolymers, polyoxyethylated polyols, polyvinyl alcohols, polysaccharides, dextrans, polyvinyl ethyl ethers, biodegradable polymers, lipid polymers, chitins, hyaluronic acids, and combinations thereof.

13. The protein conjugate according to claim 12, wherein the non-peptide polymer is polyethylene glycol.

14. The protein conjugate according to claim 1, wherein the physiologically active polypeptide is selected from the group consisting of hormones, cytokines, enzymes, antibodies, growth factors, transcription regulatory factors, coagulation factors, vaccines, structural proteins, ligand proteins and receptors.

15. The protein conjugate according to claim 14, wherein the physiologically active polypeptide is selected from the group consisting of human growth hormone, growth hormone releasing hormone, growth hormone releasing peptide, interferons, interferon receptors, colony stimulating factors, glucagon-like, G-protein-coupled receptor, interleukins, interleukin receptors, enzymes, interleukin binding proteins, cytokine binding proteins, macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors, receptor antagonists, cell surface antigens, virus derived vaccine antigens, monoclonal antibodies, polyclonal antibodies, and antibody fragments.

16. The protein conjugate according to claim 15, wherein the physiologically active polypeptide is human growth hormone, interferon-alpha, granulocyte colony stimulating factor, erythropoietin or a Fab' antibody fragment.

* * * * *